United States Patent
Akiyoshi et al.

(10) Patent No.: US 8,163,661 B2
(45) Date of Patent: Apr. 24, 2012

(54) LUMINESCENCE MEASUREMENT SYSTEM

(75) Inventors: Ryutaro Akiyoshi, Hachioji (JP);
Hirobumi Suzuki, Hino (JP)

(73) Assignee: Olympus Corporation, Tokyo (JP)

( * ) Notice: Subject to any disclaimer, the term of this patent is extended or adjusted under 35 U.S.C. 154(b) by 0 days.

(21) Appl. No.: 12/725,878

(22) Filed: Mar. 17, 2010

(65) Prior Publication Data

US 2010/0209949 A1  Aug. 19, 2010

Related U.S. Application Data

(63) Continuation of application No. PCT/JP2008/072456, filed on Dec. 10, 2008.

(30) Foreign Application Priority Data

Dec. 10, 2007 (JP) ................................ 2007-319000

(51) Int. Cl.
G01N 21/00 (2006.01)
(52) U.S. Cl. ......................................... 442/52; 382/133
(58) Field of Classification Search .............. 435/8, 189; 422/52; 436/172; 382/133
See application file for complete search history.

(56) References Cited

U.S. PATENT DOCUMENTS

| | | | |
|---|---|---|---|
| 6,416,960 B1 * | 7/2002 | Bryan | 435/7.23 |
| 2005/0144661 A1 * | 6/2005 | Piwnica-Worms et al. | 800/18 |

FOREIGN PATENT DOCUMENTS

| | | |
|---|---|---|
| JP | 2001-518799 | 10/2001 |
| JP | 2007-121837 | 5/2007 |
| JP | 2007-218774 | 8/2007 |
| WO | WO 2006/113710 A2 | 10/2006 |
| WO | WO 2007/074923 A1 | 7/2007 |

OTHER PUBLICATIONS

International Search Report dated Feb. 17, 2009.

* cited by examiner

*Primary Examiner* — Ralph Gitomer
(74) *Attorney, Agent, or Firm* — Scully, Scott, Murphy & Presser, P.C.

(57) ABSTRACT

Disclosed is a luminescence measuring method which can produce a luminous intensity depending on the amount of a substance to be measured even when the substance occurs in a biological sample in an amount equal to or more than a given amount, and which can achieve quantitative measurement. The method is characterized by includes preparing a biological sample containing a luminescence-associated protein which is can react with a substance occurring in the biological sample in amount equal to or more than a given amount and which has a Km value equal to or higher than a predetermined value so that the luminous intensity can be quantified depending on the amount of the substance, measuring the luminescence intensity emitted from the biological sample, and outputting a result of the measurement on a regions and/or part of the biological sample.

5 Claims, 28 Drawing Sheets

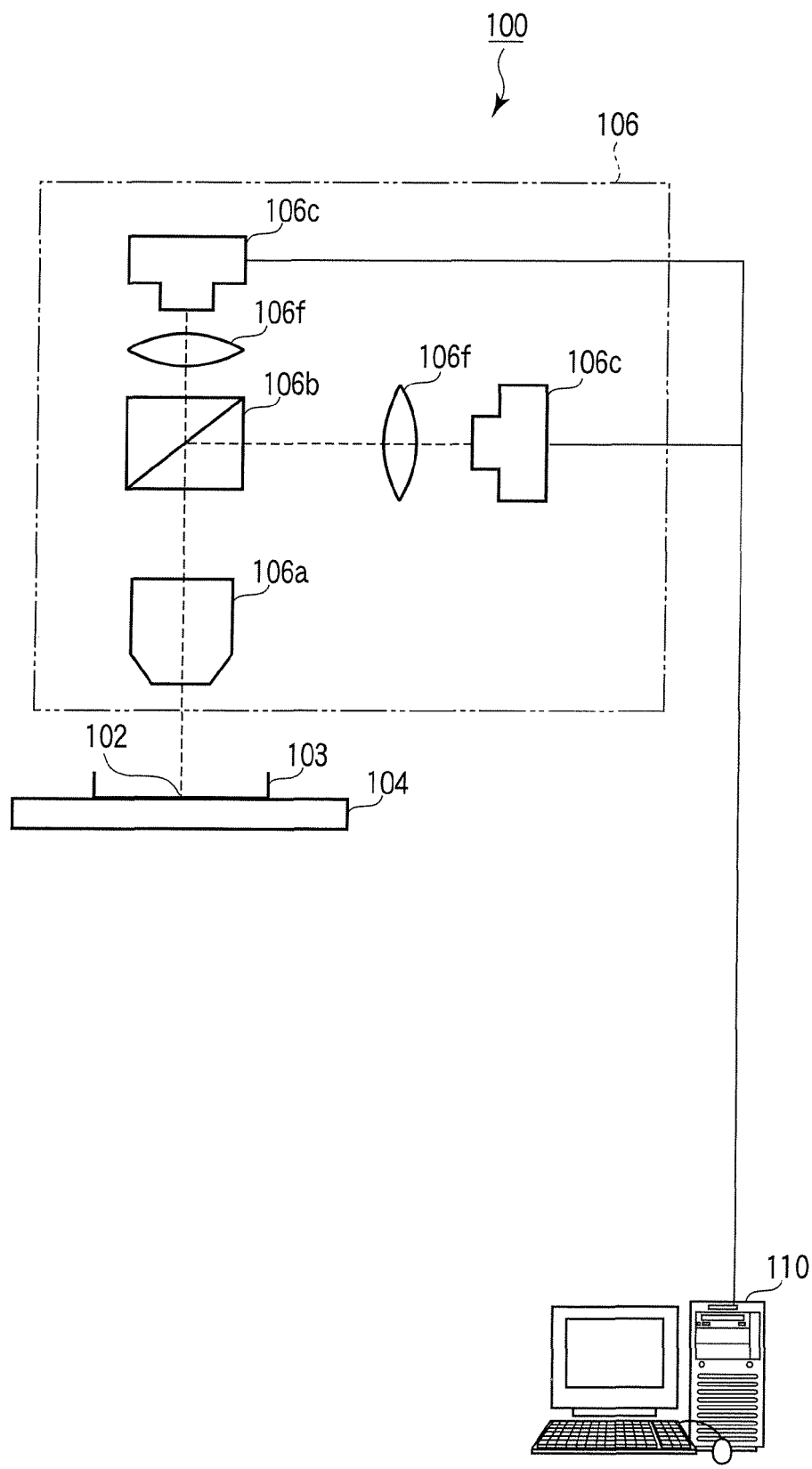
F I G. 1

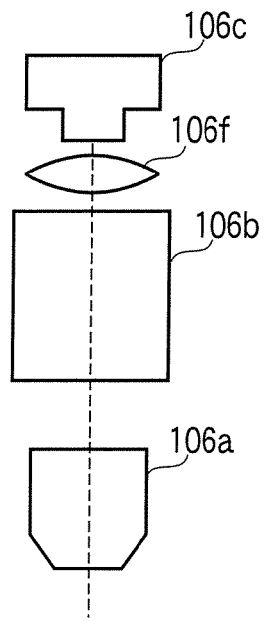
F I G. 2
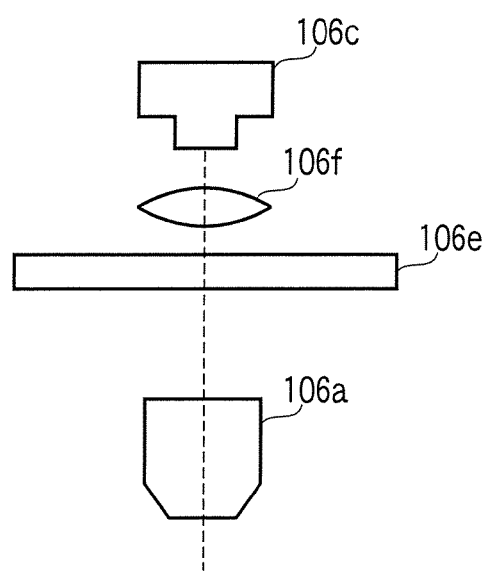
F I G. 3

| Kinds of enzyme | Km value to D-luciferin | Km value to ATP |
|---|---|---|
| CBG | 10.5 μM (10.5 μM) | 200 μM (290 μM) |
| CBR | 36.4 μM (63.8 μM) | 110 μM (130 μM) |
| ELuc | 15.0 μM (15.0 μM) | 364 μM (250 μM) |
| Genji | 75.0 μM (75.0 μM) | 500 μM (500 μM) |
| GL3 | 33.3 μM (25.0 μM) | 200 μM (200 μM) |
F I G. 5
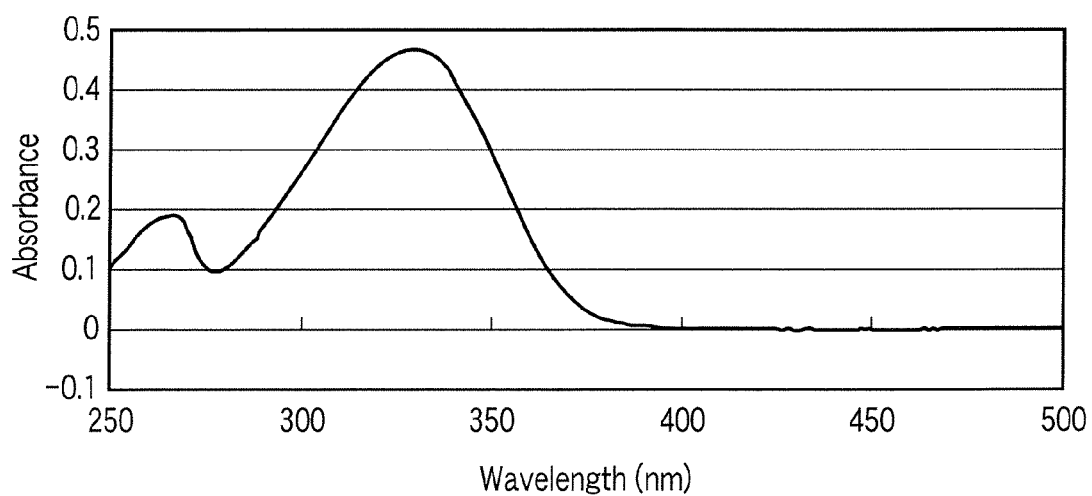
F I G. 6

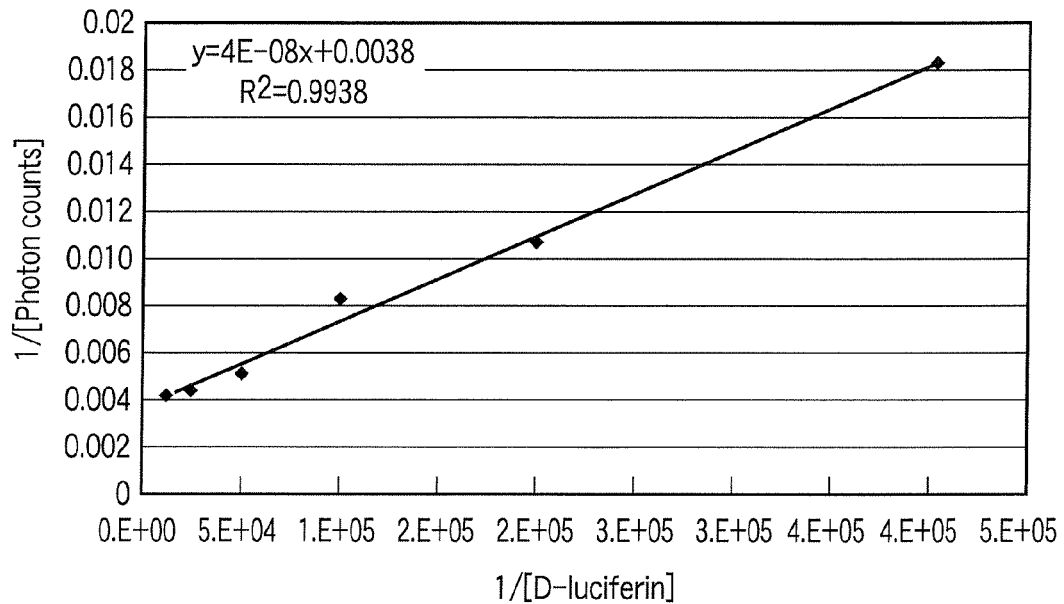
F I G. 9
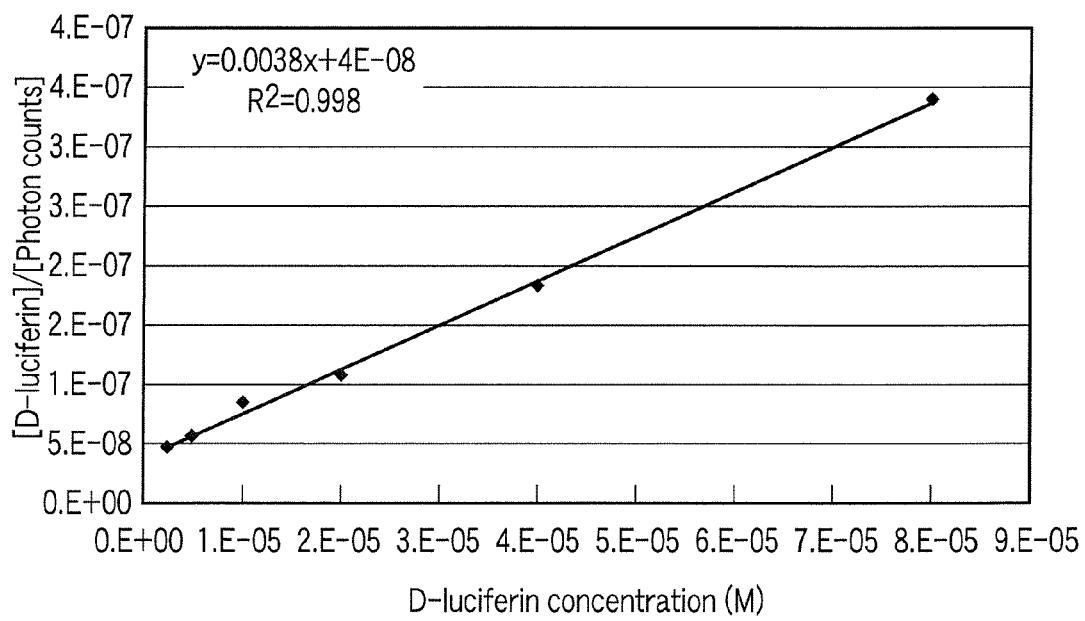
F I G. 10

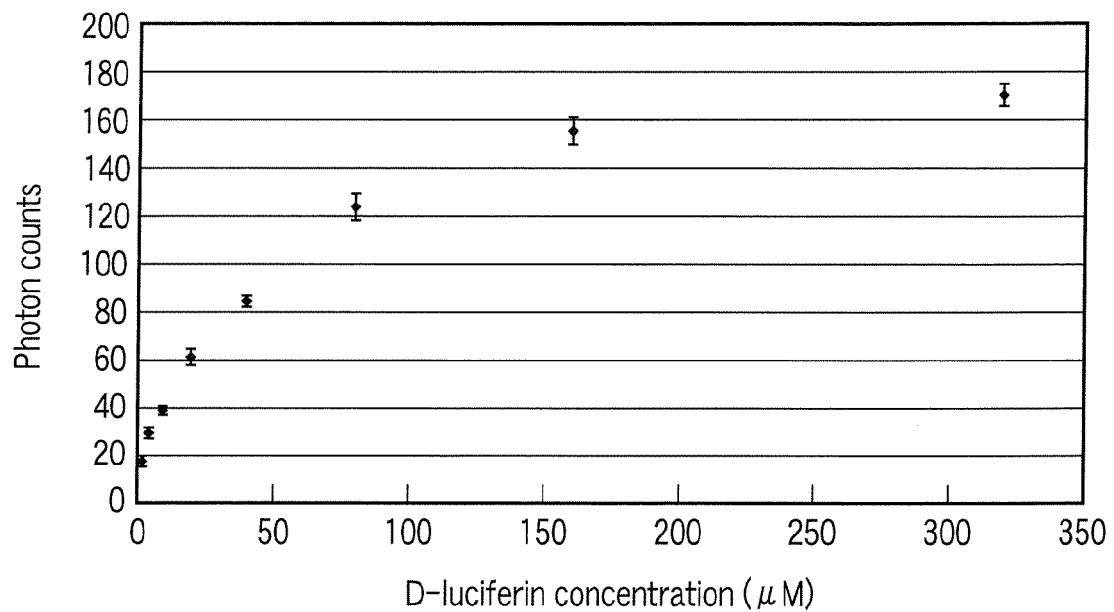
F I G. 11
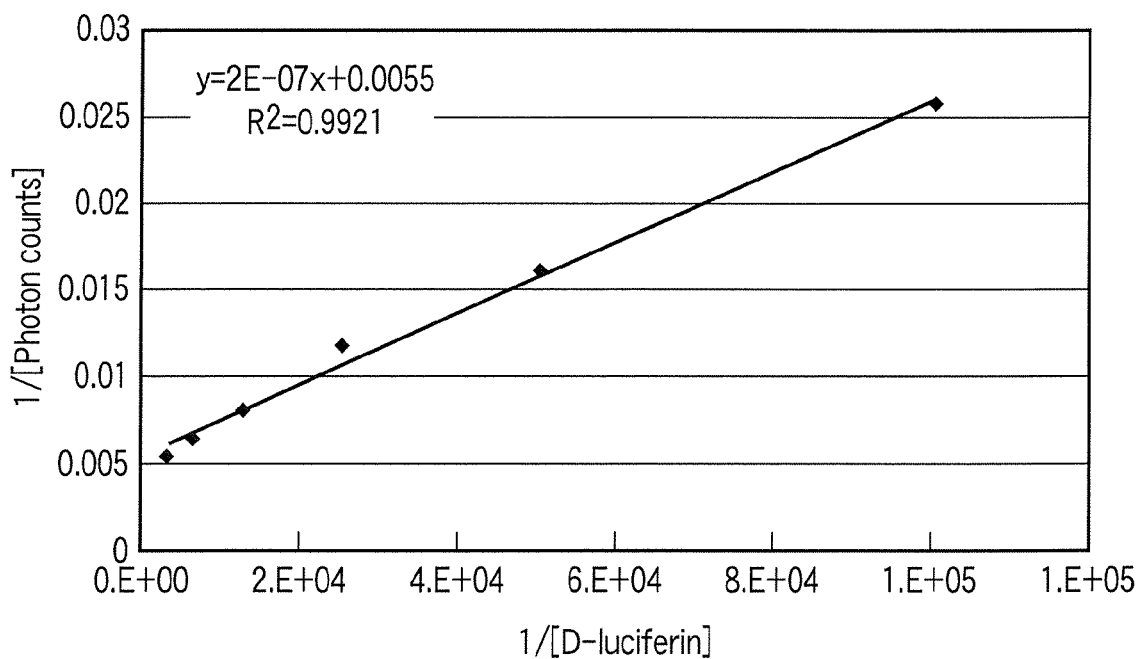
F I G. 12

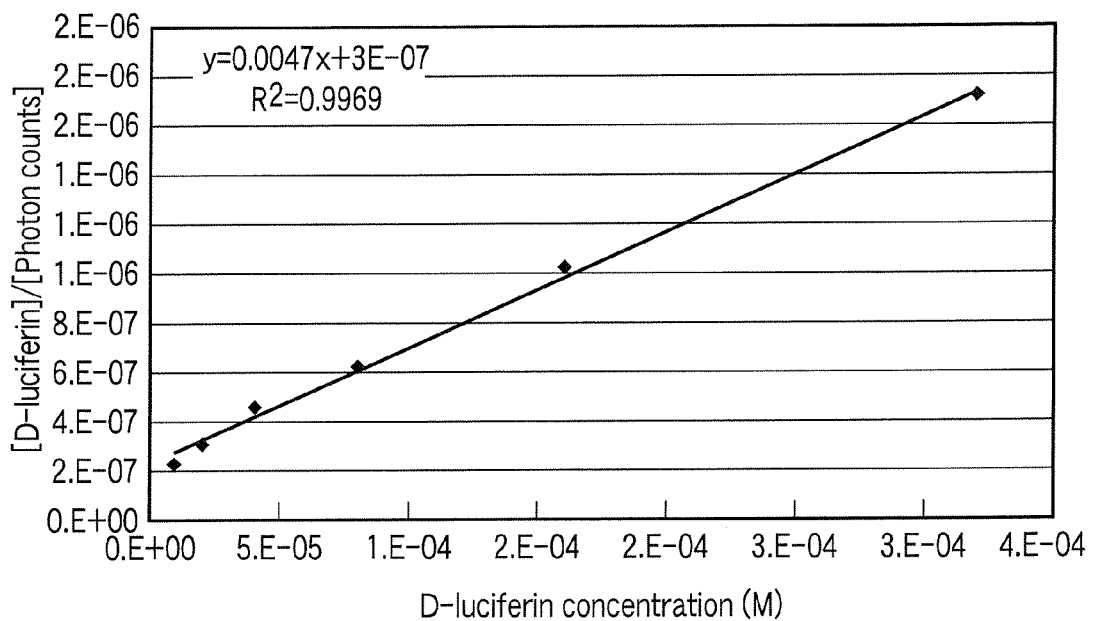
F I G. 13
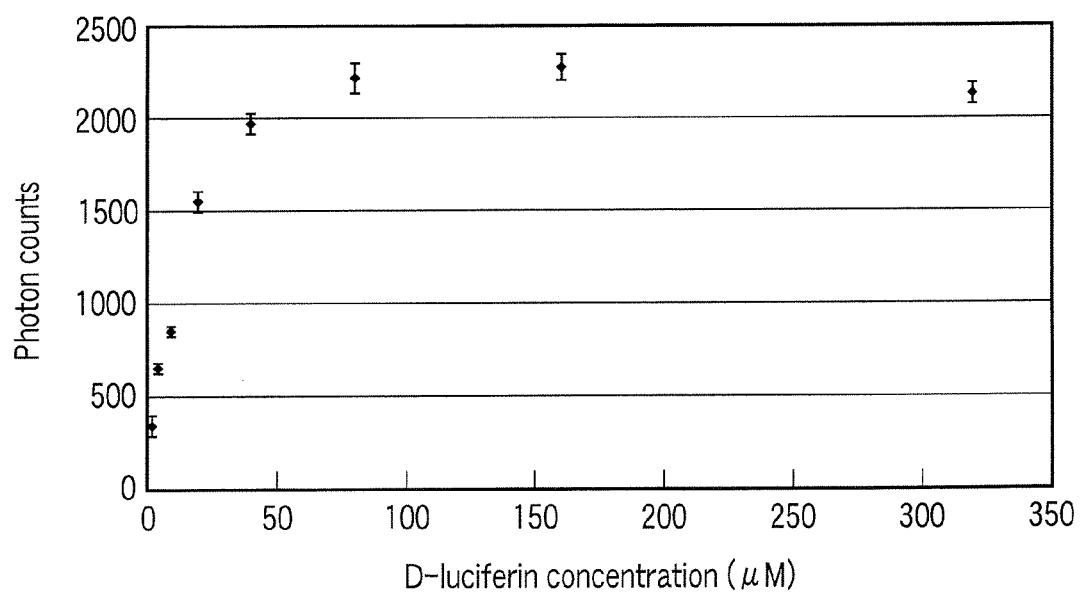
F I G. 14

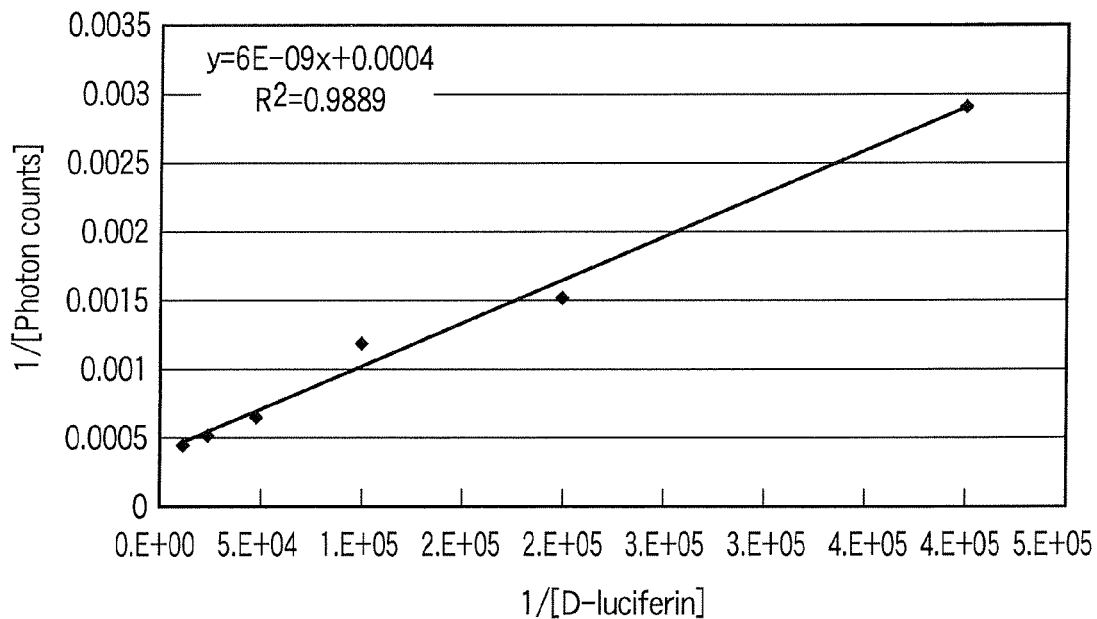
F I G. 15
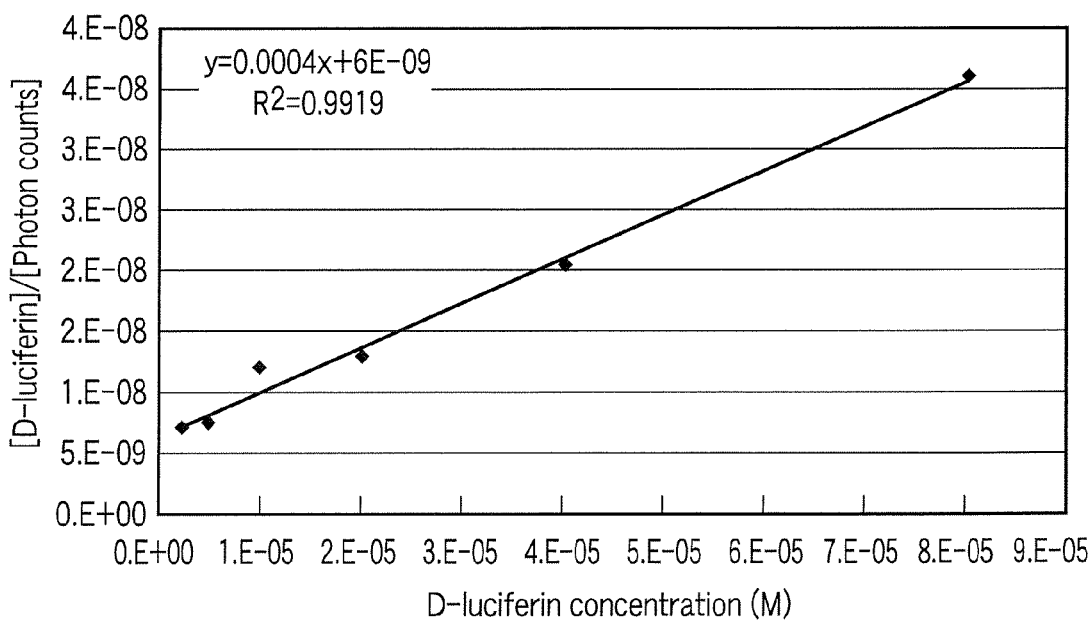
F I G. 16

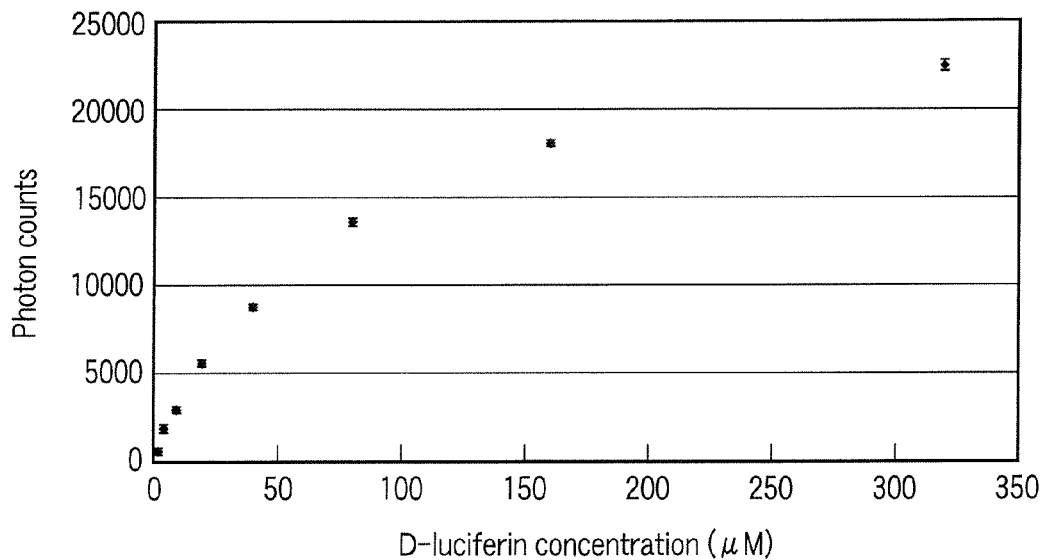
F I G. 17
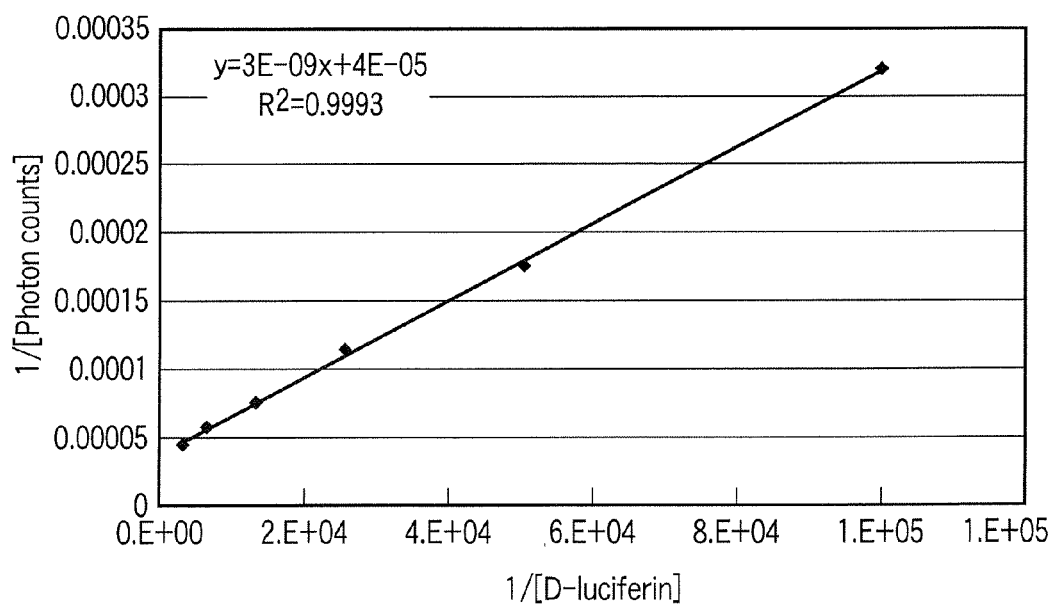
F I G. 18

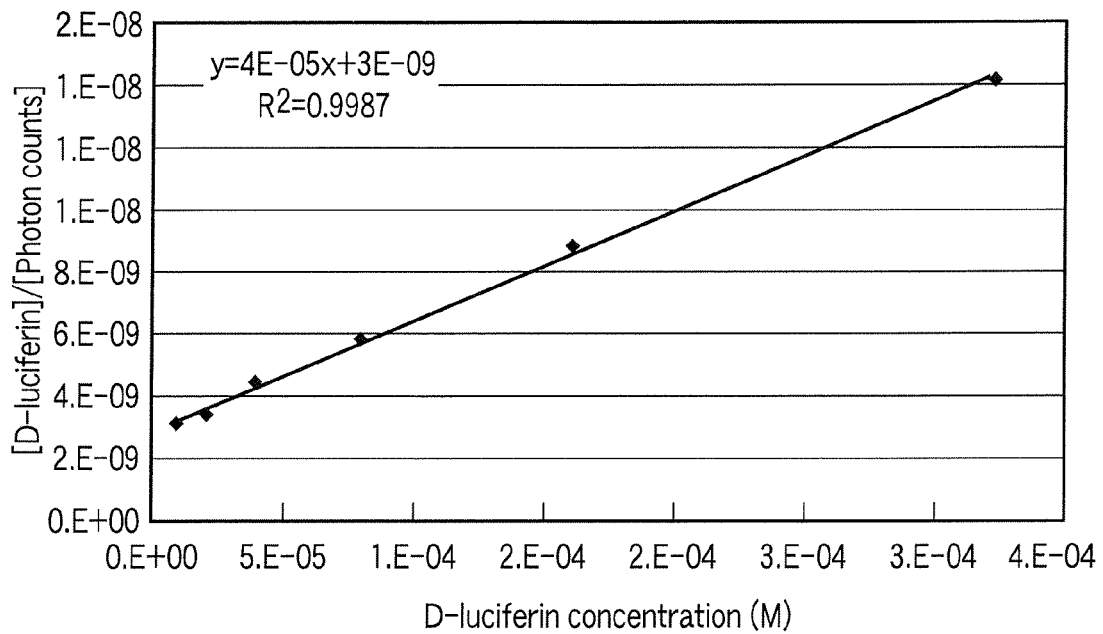
F I G. 19
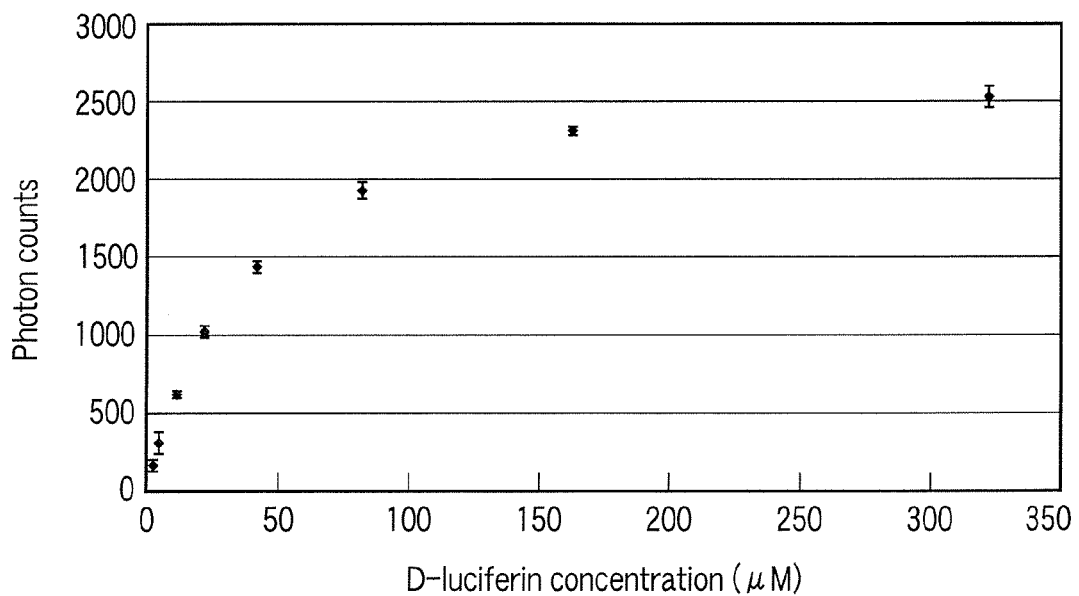
F I G. 20

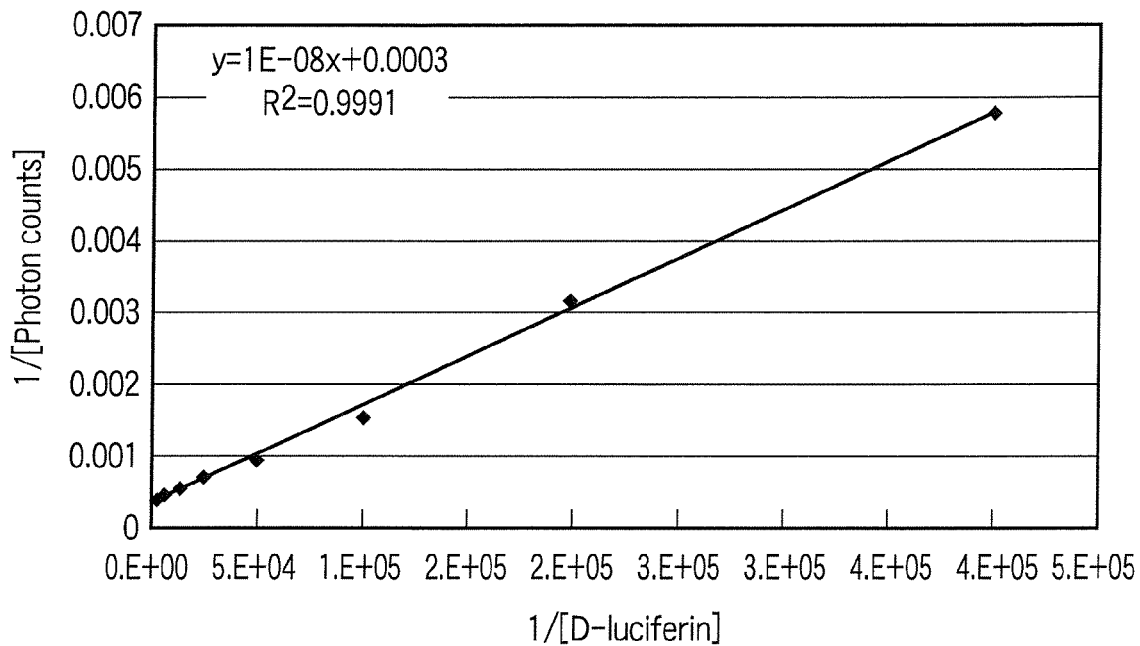
F I G. 21
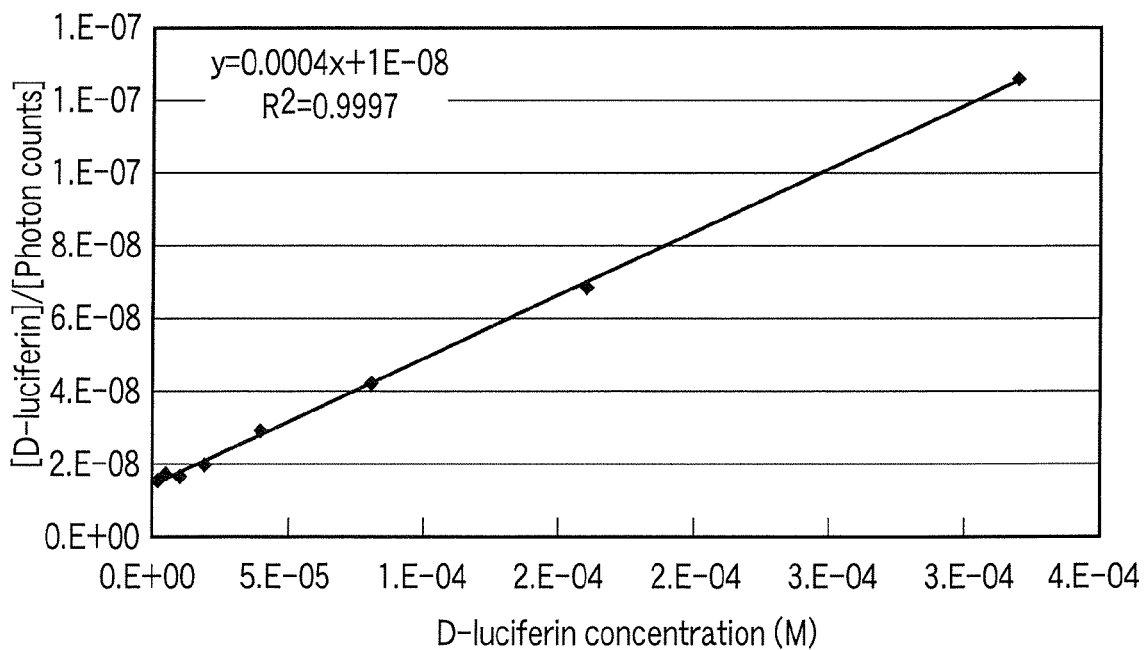
F I G. 22

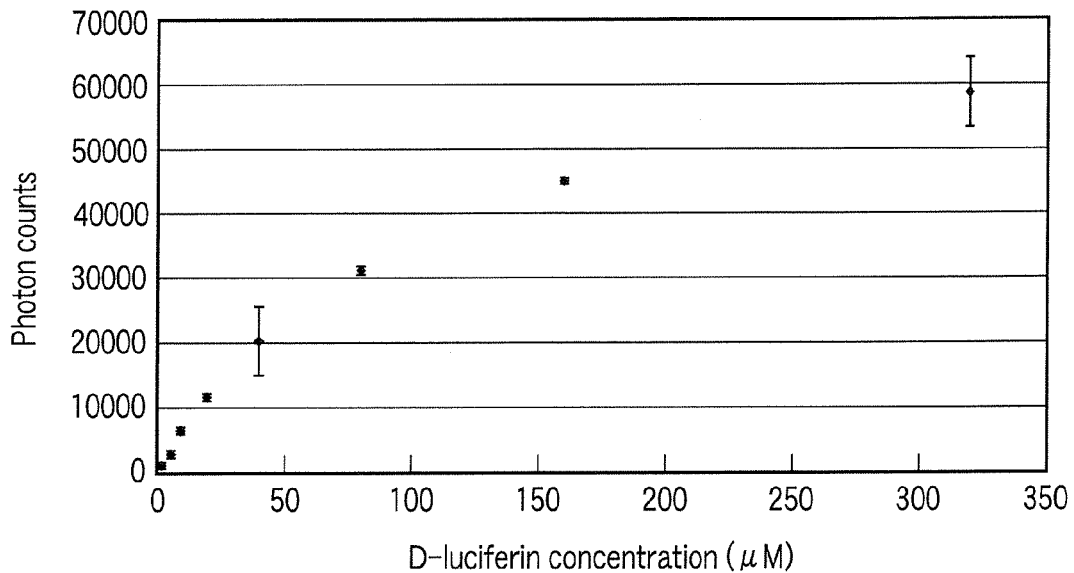
F I G. 23
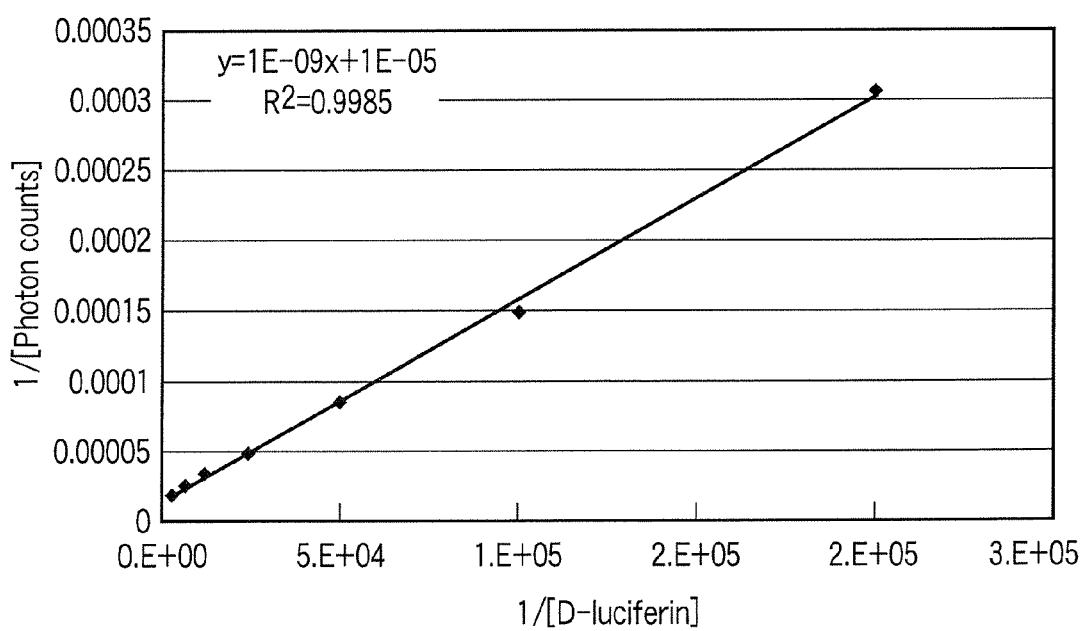
F I G. 24

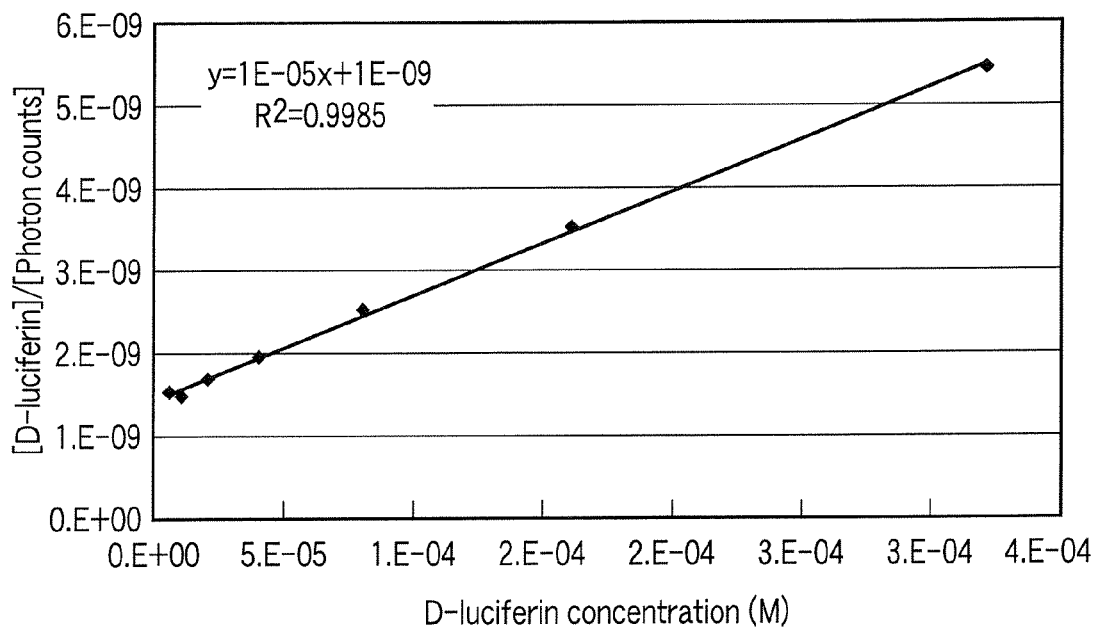
F I G. 25
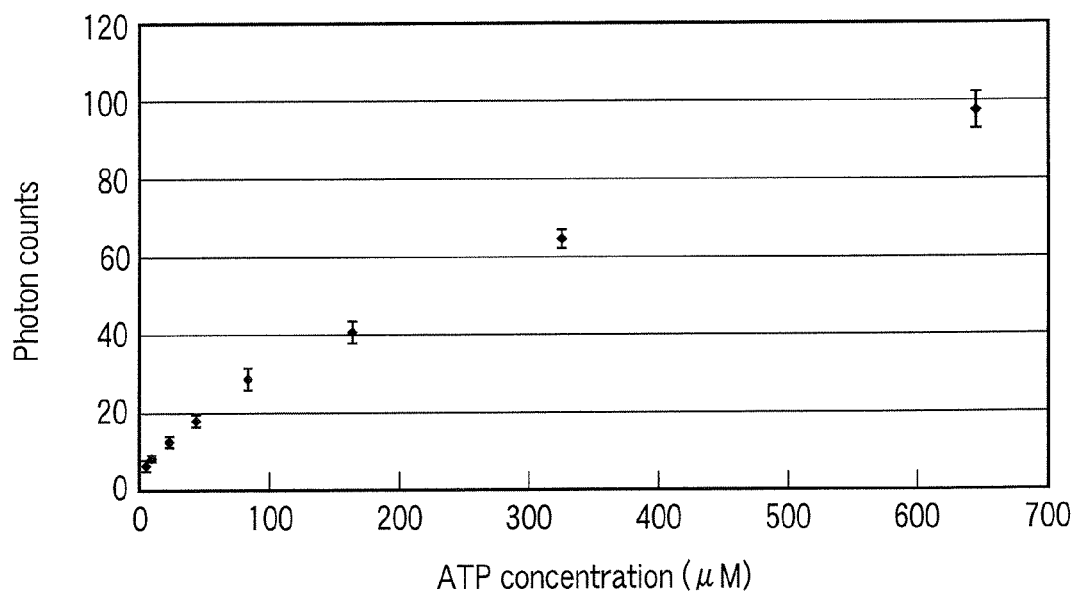
F I G. 26

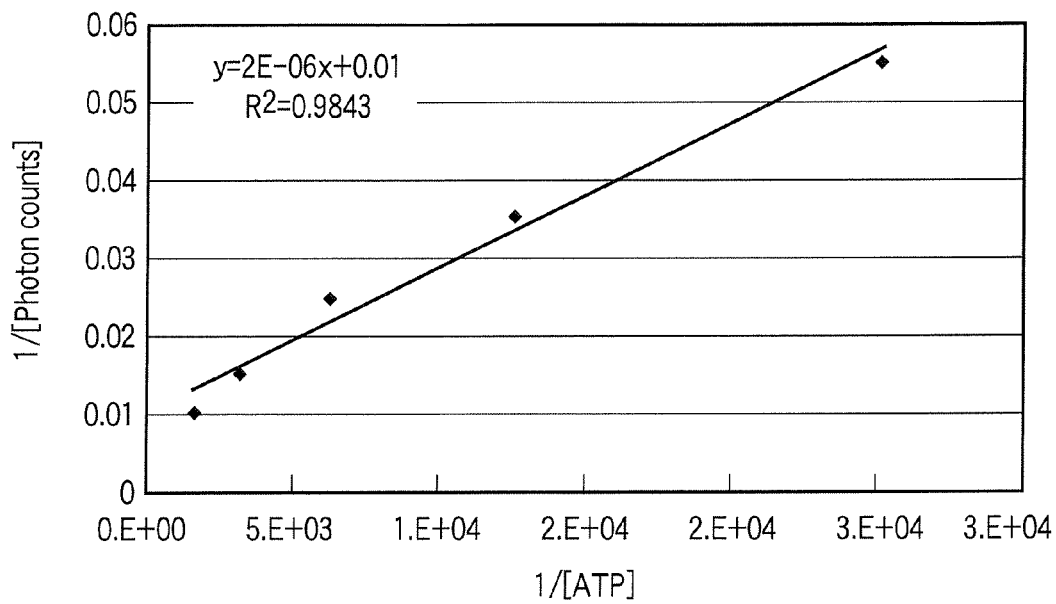
F I G. 27
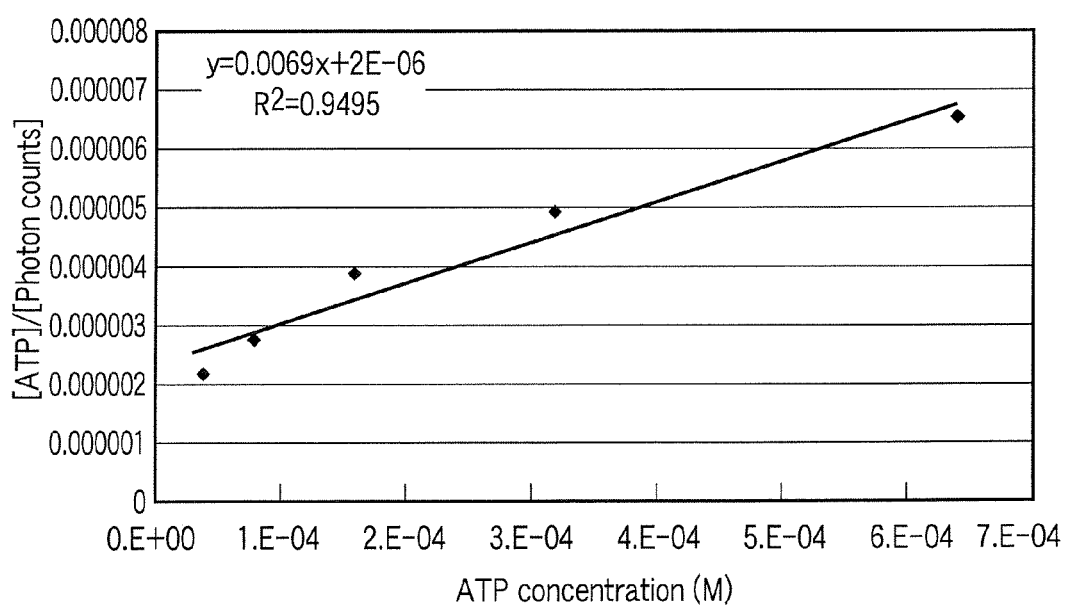
F I G. 28

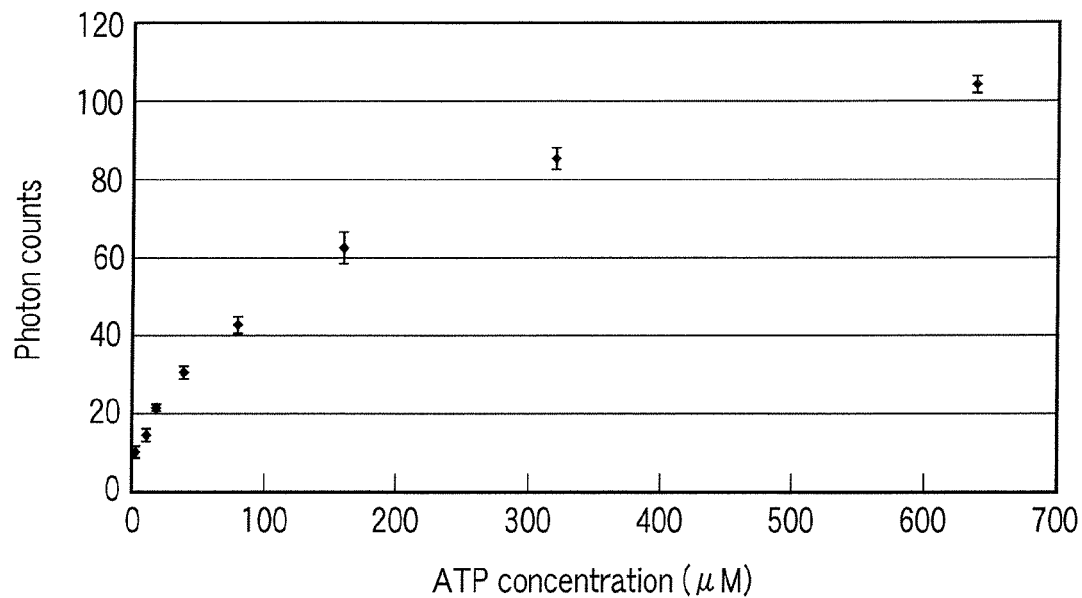
F I G. 29
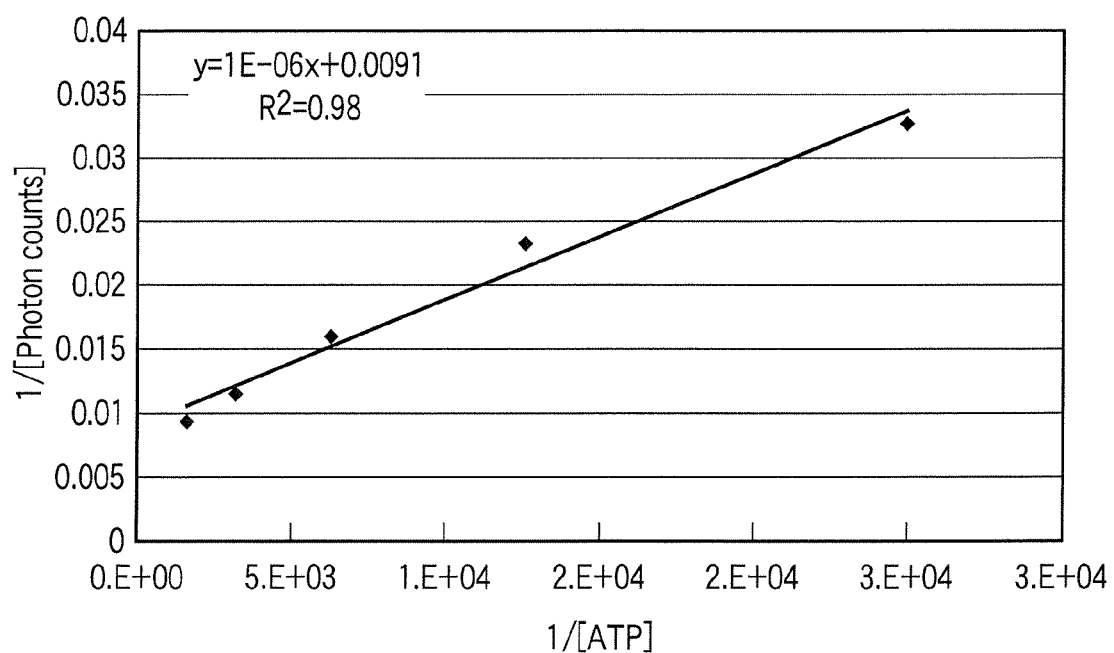
F I G. 30

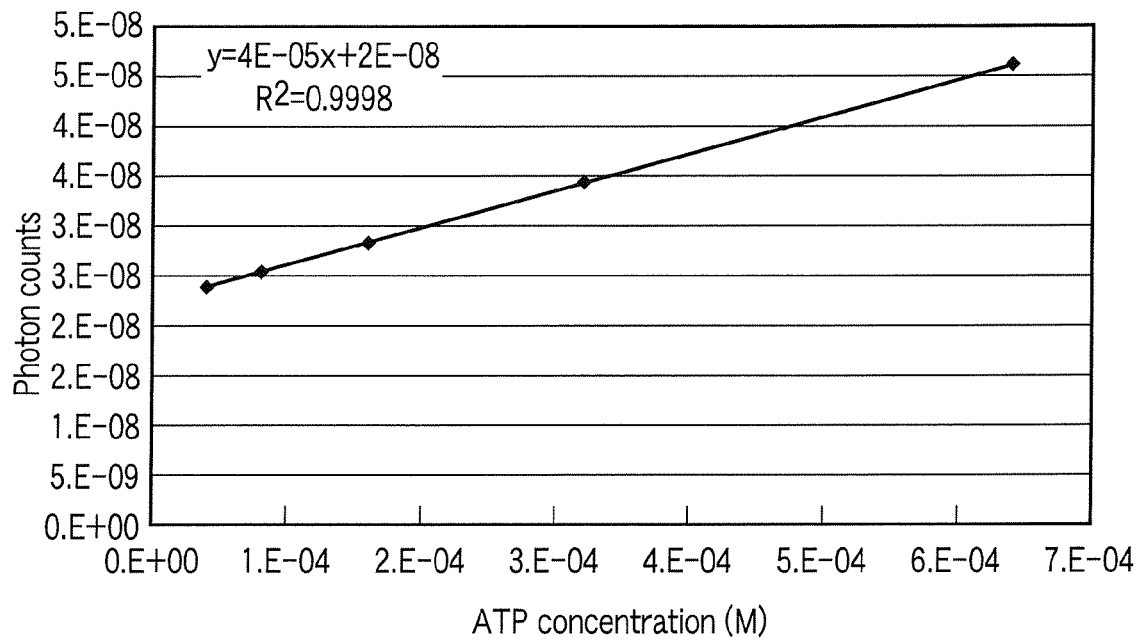
F I G. 37
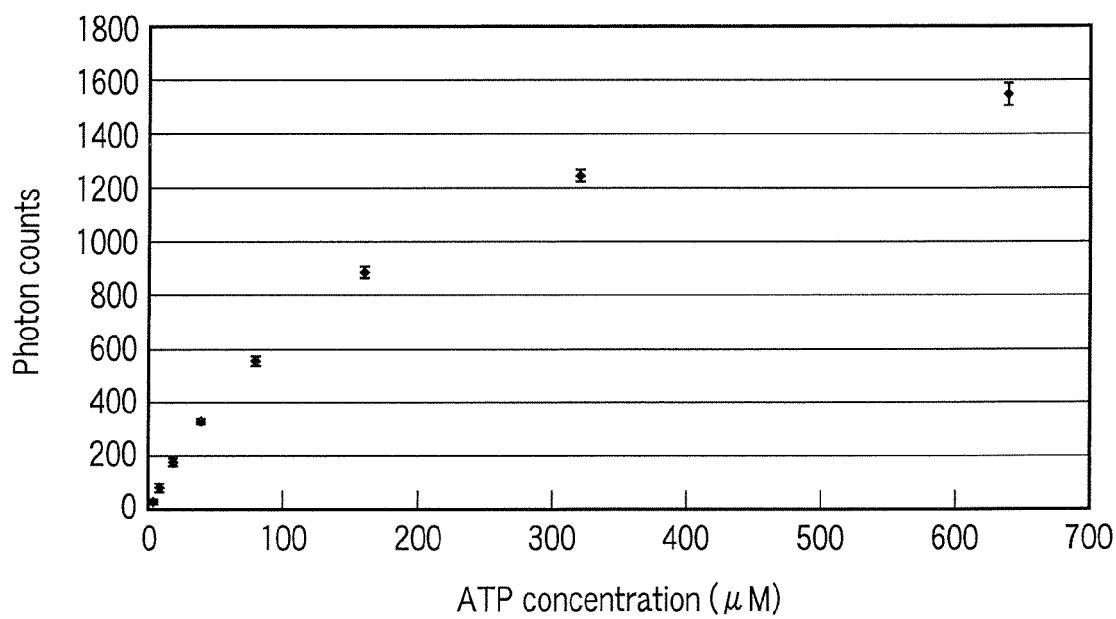
F I G. 38

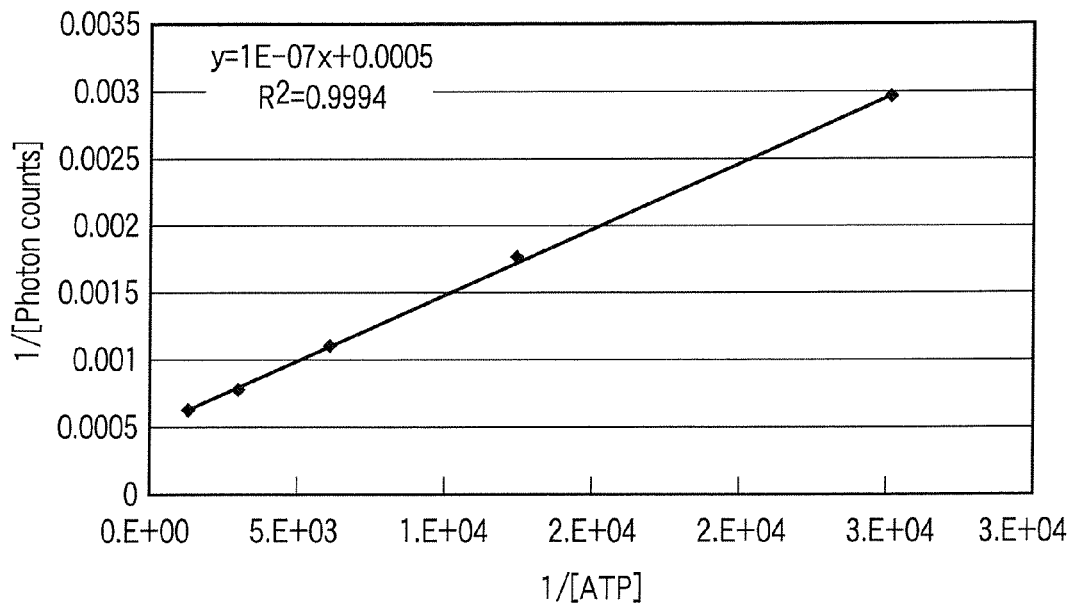
F I G. 39
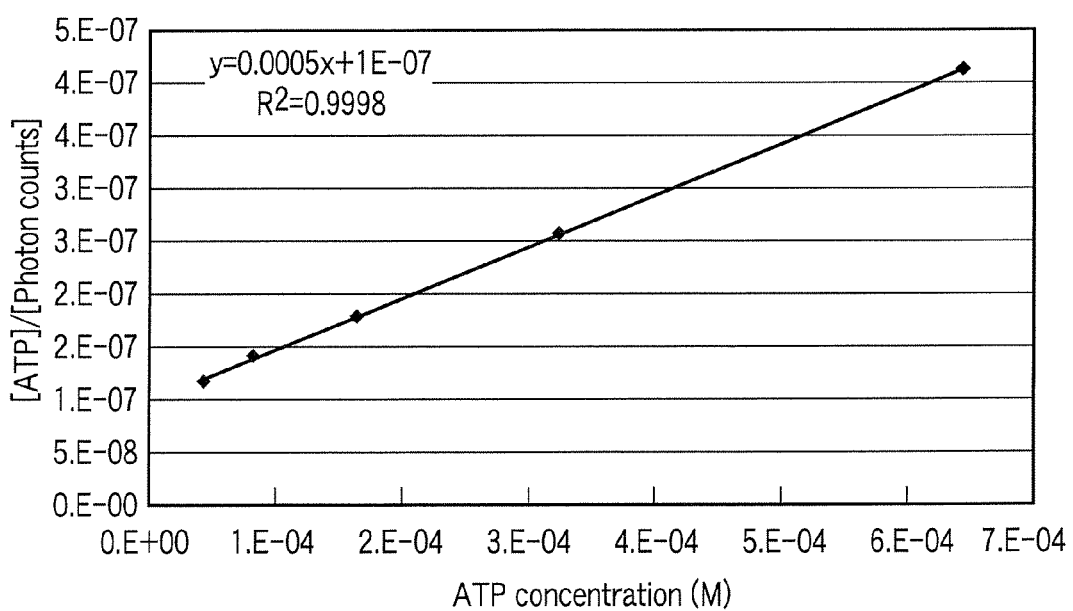
F I G. 40

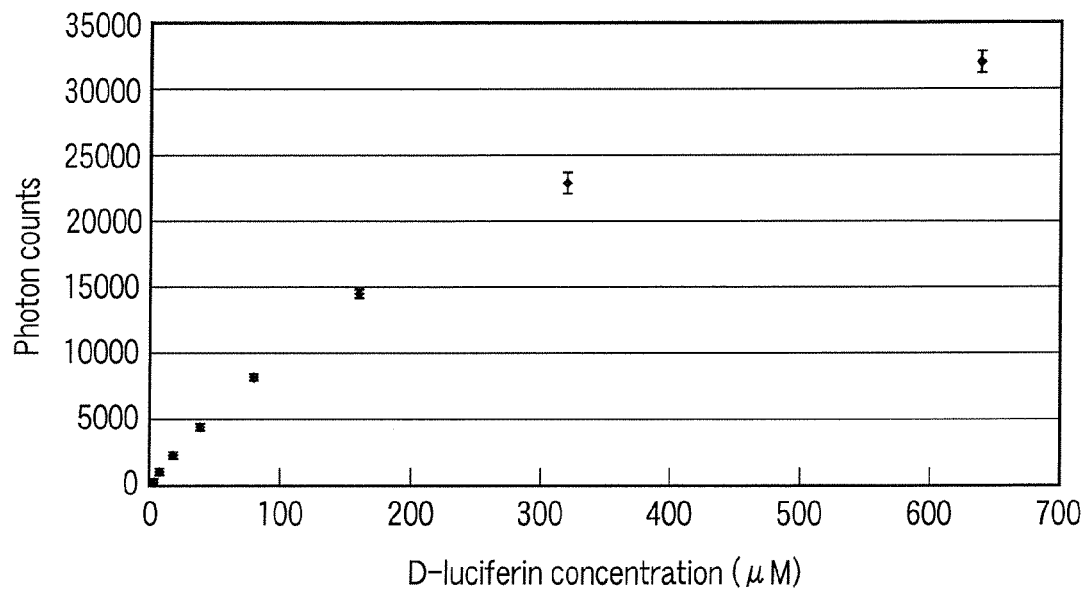
F I G. 41
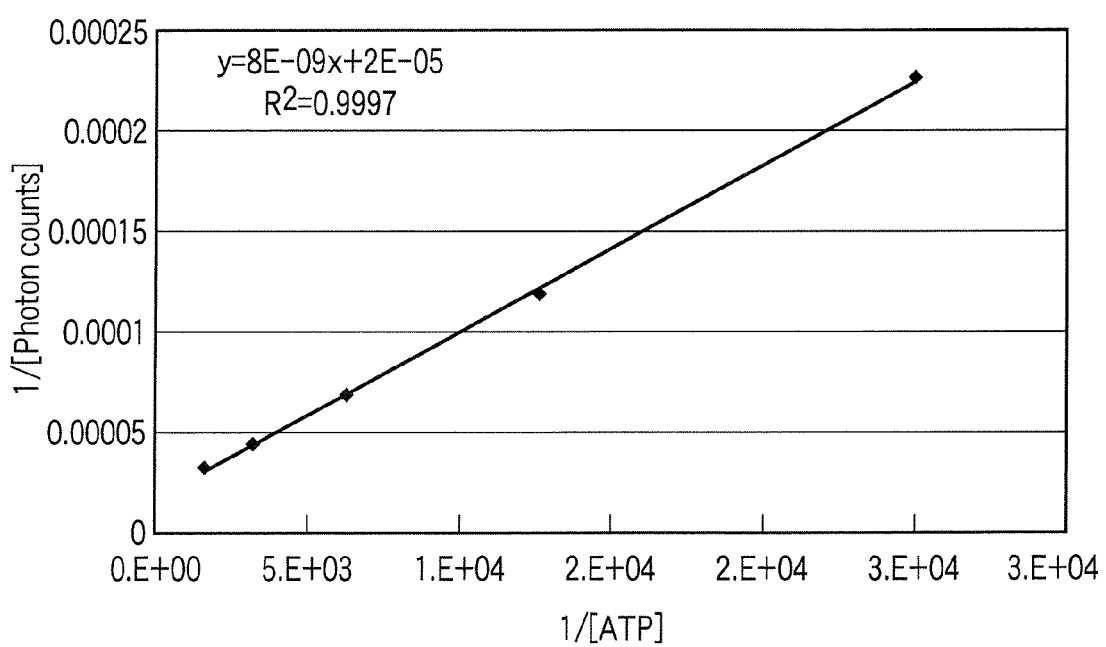
F I G. 42

| Kinds of enzyme | Km value to D-luciferin | Km value to ATP |
|---|---|---|
| CBG | 10.5 $\mu$M (10.5 $\mu$M) | 200 $\mu$M (290 $\mu$M) |
| CBR | 36.4 $\mu$M (63.8 $\mu$M) | 110 $\mu$M (130 $\mu$M) |
| ELuc | 15.0 $\mu$M (15.0 $\mu$M) | 364 $\mu$M (250 $\mu$M) |
| Genji | 75.0 $\mu$M (75.0 $\mu$M) | 500 $\mu$M (500 $\mu$M) |
| GL3 | 33.3 $\mu$M (25.0 $\mu$M) | 200 $\mu$M (200 $\mu$M) |
| Yaeyama | 100 $\mu$M (100 $\mu$M) | 400 $\mu$M (400 $\mu$M) |

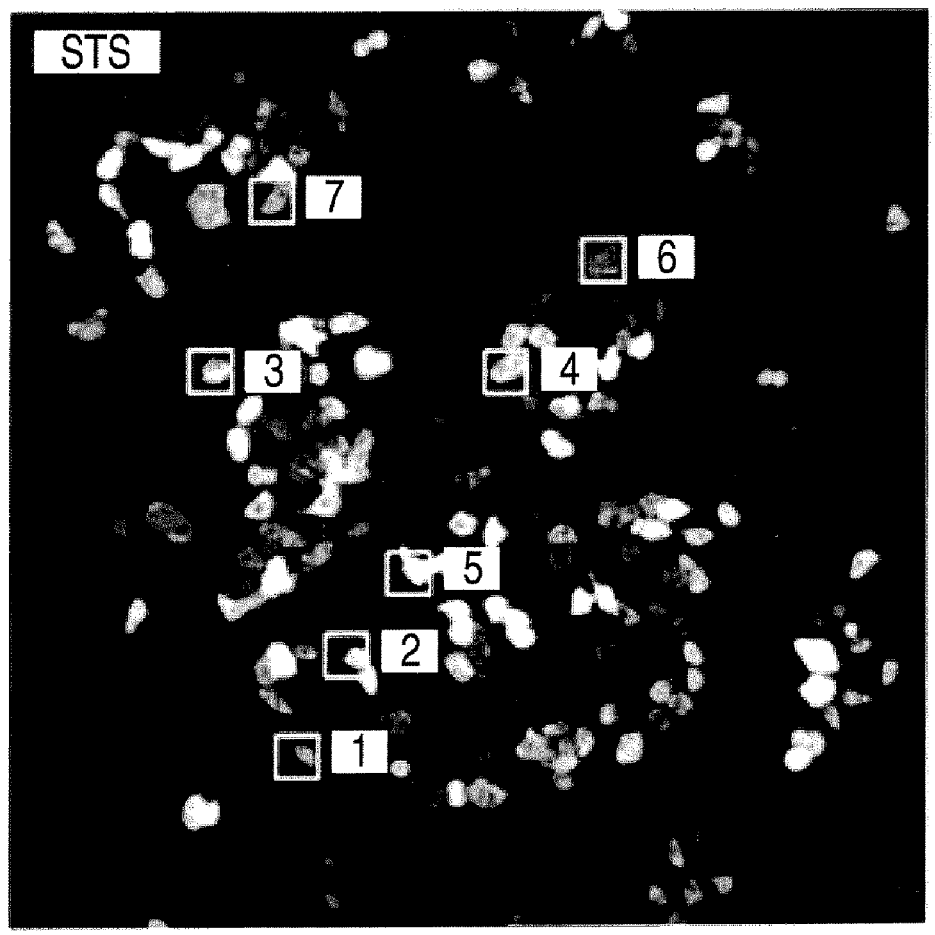
F I G. 47

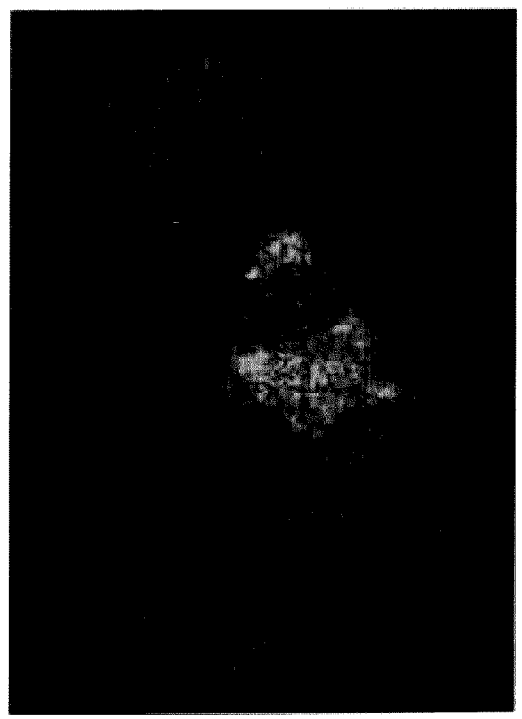
F I G. 49
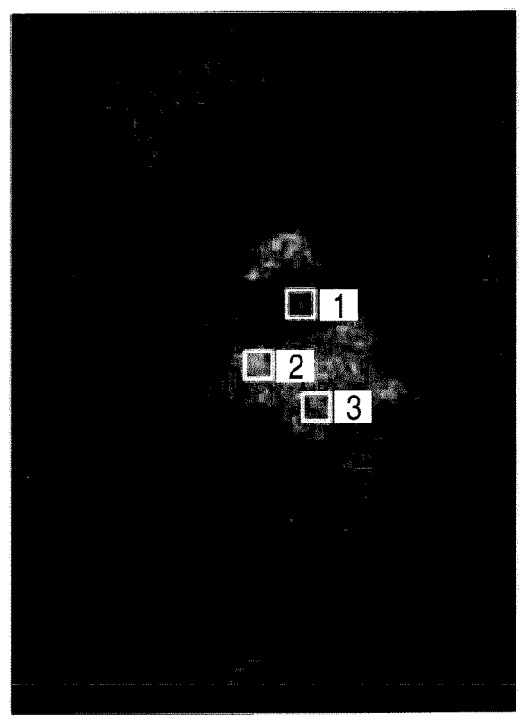
F I G. 50

LUMINESCENCE MEASUREMENT SYSTEM

CROSS-REFERENCE TO RELATED APPLICATIONS

This is a Continuation Application of PCT Application No. PCT/JP2008/072456, filed Dec. 10, 2008, which was published under PCT Article 21 (2) in Japanese.

This application is based upon and claims the benefit of priority from prior Japanese Patent Application No. 2007-319000, filed Dec. 10, 2007, the entire contents of which are incorporated herein by reference.

BACKGROUND OF THE INVENTION

1. Field of the Invention

This invention relates to a luminescence measurement method and a luminescence measurement system for observing biological samples (for example, samples including cells). In particular, this invention relates to a method and a luminescence measurement system for performing the quantitative measurement of substances that may exist excessively in a biological sample.

2. Description of the Related Art

Conventionally, luciferase which is a luminescence enzyme or GFP which is a fluorescence enzyme has been employed in a biological function analysis. In particular, an assay utilizing the luminescence from a luciferin-luciferase reaction, etc. is widely employed as an experimental technique since the assay is advantageous, as compared with the method of employing fluorescence, in many respects such as (1) excellent S/N ratio; (2) excellent quantitative performance; (3) non-cytotoxicity in the employment of exciting light; etc.

For example, the luciferase assay is employed for quantitatively measure the quantity of ATP in a biological sample by measuring the intensity of luminescence which is steadily generated by luciferase or employed for observing the level of manifestation of a specified gene through the determination of luminescence intensity that can be performed by introducing luciferase gene, together with a reporter sequence, into cells.

On this occasion, as one example of the modification of the luciferase assay, there is employed a genetic engineering method of modifying the luciferase, i.e. luminescence enzyme itself, thereby providing the luciferase with heat resistance or high luminescence properties (see Bruce R. Branchini et al. Biochemistry, 2003, 42, pp. 10429-1046).

BRIEF SUMMARY OF THE INVENTION

Problems to be Solved by the Invention

However, the conventional measuring method using a luminescence enzyme is accompanied with a problem that if a substance to be used as a substrate is existed more than a prescribed level in a biological sample, it becomes difficult to detect differences or fluctuation of luminescence intensity that will be caused in proportion to the quantity of the substrate, thereby making it difficult to quantitatively measure an object to be measured.

Especially, when it is desired to quantitatively measure ATP in an assay system utilizing a luciferin-luciferase reaction, the quantity of ATP is required to vary according to reaction rate-limiting. However, as the quantity of ATP becomes close to a state of saturation relative to luciferase, it becomes difficult to obtain an ATP-dependent luminescence intensity.

Further, when the substance to be used as a substrate is existed excessively relative to a luminescence enzyme, a difference in luminescence intensity relative to the luminescence intensity to be brought about by the manifestation of gene is caused to generate extremely, thereby bringing about a problem that it becomes difficult to concurrently detect the quantity of the substance (for example, within the same exposure time) by making use of the same device which is designed to detect a very weak beam.

The present invention has been accomplished in view of the aforementioned circumstances and, therefore, objects of the present invention are to provide a luminescence measurement method and a luminescence measurement system, which are capable of obtaining luminescence intensity in proportion to the quantity of an object substance even in a case where the object substance is existed more than a prescribed level in an biological sample, thereby making it possible to quantitatively measure the quantity of the object substance. Further objects of the present invention are to provide a luminescence measurement method and a luminescence measurement system, which are capable of overcoming the aforementioned problem of the generation of extreme difference in luminescence intensity, thereby making it possible to concurrently detect the quantity of an object substance existing more than a prescribed level in an biological sample by making use of the same device which is designed to detect a very weak beam.

Means for Solving the Problems

As a result of extensive studies performed by the present inventor, it has been found out that it is possible to more accurately measure the quantity of an object substance by selectively employing a luminescence-associated material which is low in affinity to the object substance provided that the object substance such as ATP is existed more than a prescribed level in a biological sample (for example, in cells). Especially, it has been found possible to obtain an object-depending luminescence intensity by suitably selecting a luminescence-associated material which is high in a Km value so as to prevent the concentration of the substance from approaching to the vicinity of Vmax in the Michaelis-Menten equation on the occasion of quantitatively measuring an object substance such as ATP. Further, with regard to the sequence of gene, it has been found out that Genji firefly (scientific name: Luciola cruciata; the name of luciferase thereof is referred to as Genji in this specification) among several kinds of firefly belonging to Luciola which are known to exist in the territory of Japan exhibits a difference in Km value as described in the experiments conducted as an embodiment of the present invention. The employment of luciferase as a luminescence marker in conformity with the intended purpose by taking advantage of this difference in Km value is one of the important subject matters of the present invention.

Namely, to solve the problems mentioned above and achieve the objectives, the luminescence measuring method for measuring luminescence emitted from a biological sample according to the present invention is characterized by comprising the step of preparing a biological sample containing a luminescence-associated protein which is capable of reacting with a substance existing more than a prescribed quantity in the biological sample, the protein having a Km value which is higher than a prescribed value which enables to quantitatively measure a luminescence intensity in dependence with the substance, the step of measuring the luminescence intensity emitted from the biological sample prepared in above-described preparing step and the step of outputting a measured result obtained from each of regions and/or sites of the biological sample, that is, a measured result in regard to the luminescence intensity obtained in above-described measuring step.

Further, the luminescence measuring method according to the present invention is characterized by the substance being ATP, the luminescence-associated protein being luciferase, and the Km value being not less than 364.

Further, the luminescence measuring method according to the present invention is characterized by the luciferase being Yaeyama Hime firefly-originated luciferase to be created based on the DNA sequence of Sequence No. 1.

Further, the luminescence measuring method according to the present invention is characterized by the step of measurement including a step of picking up a luminescence image based on the biological luminescence of the biological sample including a plurality of cells.

Further, the luminescence measuring method according to the present invention is characterized by the step of measurement including a step of measuring the luminescence intensity of each of the cells.

Further, the luminescence measuring method according to the present invention is characterized by the step of preparation comprising a step of preparing the biological sample by making use of a plurality of luminescence-associated proteins differing in the Km value from each other.

Further, the luminescence measuring method according to the present invention is characterized by the step of measurement being performed depending on the Km value.

Further, the luminescence measuring method according to the present invention is characterized by the step of output being performed depending on the Km value.

Moreover, the present invention is a luminescence measurement system for executing the luminescence measuring methods mentioned above, the system is characterized by comprising a picking up section for obtaining luminescent image from a biological sample, an image analysis section for executing image processing for analyzing the luminescent image obtained from the picking up section, an output device for outputting a result of the analysis of image obtained from the image analysis section, and a dynamic range adjusting section for executing the picking up section and the image analysis section in conformity with the Km value of luminescent protein used in the biological sample.

Further, in the luminescence measurement system according to the present invention, it is characteristic that the dynamic range adjusting section is provided with a plurality of control modes.

Moreover, in the luminescence measurement system according to the present invention, it is characteristic that the system further comprises an input device for designating a desired region and/or a desired site in the biological sample, and a memory section for storing information input from the input device, wherein the dynamic range adjusting section is designed to output an output content in which an image and an analyzed image are formulated in conformity with the information stored in the memory section (in correspondence with the dynamic range, the picking up section and the image analysis section execute the processing based on information stored in a memory section, and an output apparatus outputs the results of imaging corresponding to the information to be output).

Effects to be Obtained from The Invention

According to the method of the present invention, a biological sample containing a luminescence-associated protein is prepared. In this case, the protein which is capable of reacting with a substance existing more than a prescribed level in the biological sample and which has a higher Km value than a predetermined level is selected, thereby making it possible to quantitatively measure luminescence intensity in proportion to the quantity of the substance. Then, the luminescence intensity to be generated from the biological sample thus prepared is measured, thus making it possible to output measured results of each of region and/or site of the biological sample. By doing so, it is possible to perform quantitative measurement in proportion to the quantity of the substance even in a case where the substance to be measured is existed more than a prescribed level in the biological sample. Further, since it is possible to adjust the luminescence intensity so as to prevent the generation of an extreme difference in luminescence intensity, it is possible to realize the merit that the examination of many items can be concurrently performing by making use of the same very weak beam detecting apparatus. Furthermore, it is also possible to realize the merit that a plurality of regions of a biological sample or a plurality of sites in the same cell can be concurrently measured and hence it is now possible to perform the analysis of each of regions (or each of sites) which are related to a luminescence picture image that has been obtained.

According to the present invention, since the substance to be measured may be ATP and the luminescence-associated protein may be luciferase and the Km value is not less than 364 μM, it is possible to realize the merit that ATP can be rate-determined, thus making it possible to obtain a quantitative luminescence intensity depending on the existence of ATP.

According to the present invention, since the luciferase originated from Yaeyama-hime firefly that can be created based on the DNA sequence of Sequence No. 1 is employed, it is possible to realize the merit that a large ATP-dependent difference in luminescence intensity and hence a glow type luminescence pattern. Especially, as the concentration of ATP within cells is decreased by a chemical treatment from 1.35 mM to 0.65 mM, the reaction velocity is expected to decrease from about 80% of Vmax to about 60% according to Michaelis-Menten equation when luciferase (Yaeyama) originated from Yaeyama-hime firefly is employed, thereby generating a difference of 20% in the reaction velocity thus further facilitating the detection of Yaeyama as compared with the case where GL3 is employed (a difference of about 5% in reaction velocity).

According to the present invention, in the step of measuring the luminescence intensity, a luminescence picture image of biological sample containing a plurality of cells is pictured based on bioluminescence. By doing so, it is possible to obtain the merit that the regions of a plurality of cells and/or a plurality of sites within the same cell can be concurrently measured.

According to the present invention, in the step of measuring the luminescence intensity, it is performed for each one of cells. By doing so, it is possible to obtain the merit that it is possible to designate the region and/or site to be measured for each cell and to quantitatively measure a plurality of regions and sites at the same time.

According to the present invention, in the step of preparing a biological sample, the biological sample is prepared by making use of a plurality of luminescence-associated proteins differing in Km value from each other. By doing so, it is possible to obtain the merit that it is possible to perform quantitative measurement concurrently even when there is a large difference in the quantity of object substance to be measured.

According to the present invention, in the step of measuring the luminescence intensity, the measurement is performed in correspondence with the Km value. By doing so, it is possible to obtain the merit that it is possible to perform quantitative measurement by changing the intervals of image pick-up or exposure time in correspondence with the Km value of the luminescence-associated proteins. For example, the kinetic analysis as to how the dynamics of a bioactive substance which is wide in dynamic range has been changed and also the analysis of the expression/fluctuation of a specific gene as to how the transcription of the specific gene related to the dynamics of the bioactive substance has been controlled can be performed quickly or at real-time on the same cell (or cell group).

According to the present invention, in the step of outputting the results of analysis, the out is executed in correspondence with the Km value. By doing so, it is possible to obtain the merit that the results of analysis can be output after they have been subjected to conversion processing based on various parameters (coloration, contrast, dimension, display speed of moving images, etc.) in conformity with the dynamic range based on the Km value.

According to the present invention, a luminescent picture image to be derived from a biological sample is obtained in correspondence with the Km value of luminescent protein used in the biological sample and the image processing for analyzing the luminescent picture image is performed in correspondence with the Km value of luminescent protein used in the biological sample before outputting the results of the image analysis. By doing so, it is possible to obtain the merit that a plural kinds of measurement differing in dynamic range from each other in correspondence with Km value can be carried out to the same or different objects to be analyzed.

According to the present invention, the adjustment of dynamic range having a plurality of control modes is performed. By doing so, not only a measuring item having a wide dynamic range such as ATP but also a measuring item having a relatively narrow dynamic range such as the expression of a specific gene, for example, can be carried out to the same object to be analyzed, thereby making it possible to track concurrently or at real-time each of regions and/or sites on the same picture image.

According to the present invention, a desired region and/or site in a biological sample is designated through an input apparatus, and information that has been input by the input apparatus is stored in a memory section, after which, based on the information stored in the memory section, the image pick-up section and the image analysis section are actuated by means of the dynamic range adjustment section, thereby enabling the results of imaging corresponding to the information to be output by means of an output apparatus. By doing so, it is possible to obtain the merit that the dynamic range can be adjusted in conformity with the Km value of luminescence-associated proteins so as to carry out the image pick-up processing, analytical processing and output processing in correspondence with the dynamic range, thereby enabling a plural kinds of measurement differing in dynamic range from each other in correspondence with Km value to be carried out to the same or different objects to be analyzed.

BRIEF DESCRIPTION OF THE SEVERAL VIEWS OF THE DRAWING

FIG. 1 is a diagram illustrating one example of the overall construction of a luminescence observation system 100;

FIG. 2 is a diagram illustrating one example of the construction of a luminescent image pick-up unit 106 of the observation system 100;

FIG. 3 is a diagram illustrating another example of the construction of a luminescent image pick-up unit 106 of the observation system 100;

FIG. 5 is a table showing the Km value of D-luciferase and the Km value of various kinds of luciferase to ATP;

FIG. 6 is a graph showing the ultraviolet/visible light absorption spectrum of D-luciferase;

FIG. 9 is a graph showing Lineweaver-Burk plots obtained relative to the concentration of D-luciferase of CBG;

FIG. 10 is a graph showing Hanes-Woolf plots obtained relative to the concentration of D-luciferase of CBG;

FIG. 11 is a graph showing the fluctuation of luminescence intensity due to an increase in concentration of D-luciferase of CBR;

FIG. 12 is a graph showing Lineweaver-Burk plots obtained relative to the concentration of D-luciferase of CBR;

FIG. 13 is a graph showing Hanes-Woolf plots obtained relative to the concentration of D-luciferase of CBR;

FIG. 14 is a graph showing the fluctuation of luminescence intensity due to an increase in concentration of D-luciferase of ELuc;

FIG. 15 is a graph showing Lineweaver-Burk plots obtained relative to the concentration of D-luciferase of ELuc;

FIG. 16 is a graph showing Hanes-Woolf plots obtained relative to the concentration of D-luciferase of ELuc;

FIG. 17 is a graph showing the fluctuation of luminescence intensity due to an increase in concentration of D-luciferase of Genji;

FIG. 18 is a graph showing Lineweaver-Burk plots obtained relative to the concentration of D-luciferase of Genji;

FIG. 19 is a graph showing Hanes-Woolf plots obtained relative to the concentration of D-luciferase of Genji;

FIG. 20 is a graph showing the fluctuation of luminescence intensity due to an increase in concentration of D-luciferase of GL3;

FIG. 21 is a graph showing Lineweaver-Burk plots obtained relative to the concentration of D-luciferase of GL3;

FIG. 22 is a graph showing Hanes-Woolf plots obtained relative to the concentration of D-luciferase of GL3;

FIG. 23 is a graph showing the fluctuation of luminescence intensity due to an increase in concentration of D-luciferase of Yaeyama;

FIG. 24 is a graph showing Lineweaver-Burk plots obtained relative to the concentration of D-luciferase of Yaeyama;

FIG. 25 is a graph showing Hanes-Woolf plots obtained relative to the concentration of D-luciferase of Yaeyama;

FIG. 26 is a graph showing the fluctuation of luminescence intensity due to an increase in concentration of ATP of CBG;

FIG. 27 is a graph showing Lineweaver-Burk plots obtained relative to the concentration of ATP of CBG;

FIG. 28 is a graph showing Hanes-Woolf plots obtained relative to the concentration of ATP of CBG;

FIG. 29 is a graph showing the fluctuation of luminescence intensity due to an increase in concentration of ATP of CBR;

FIG. 30 is a graph showing Lineweaver-Burk plots obtained relative to the concentration of ATP of CBR;

FIG. 37 is a graph showing Hanes-Woolf plots obtained relative to the concentration of ATP of Genji;

FIG. 38 is a graph showing the fluctuation of luminescence intensity due to an increase in concentration of ATP of GL3;

FIG. 39 is a graph showing Lineweaver-Burk plots obtained relative to the concentration of ATP of GL3;

FIG. 40 is a graph showing Hanes-Woolf plots obtained relative to the concentration of ATP of GL3;

FIG. 41 is a graph showing the fluctuation of luminescence intensity due to an increase in concentration of ATP of Yaeyama;

FIG. 42 is a graph showing Lineweaver-Burk plots obtained relative to the concentration of ATP of Yaeyama;

FIG. 47 is a photograph showing a picture of luminescence image taken immediately after the stimulation using chemicals in an ELuc-expressing HeLa cell;

FIG. 49 is a photograph showing one example of the luminescent image photographed prior to the stimulation (before the Apoptosis induction by way of the stimulation of cell), which was performed according to the process and conditions of experiment performed in Example 4;

FIG. 50 is a photograph showing an image obtained as three measurement regions (ROI: region of interest) were designated in the luminescent image shown in FIG. 49.

Figure 4:
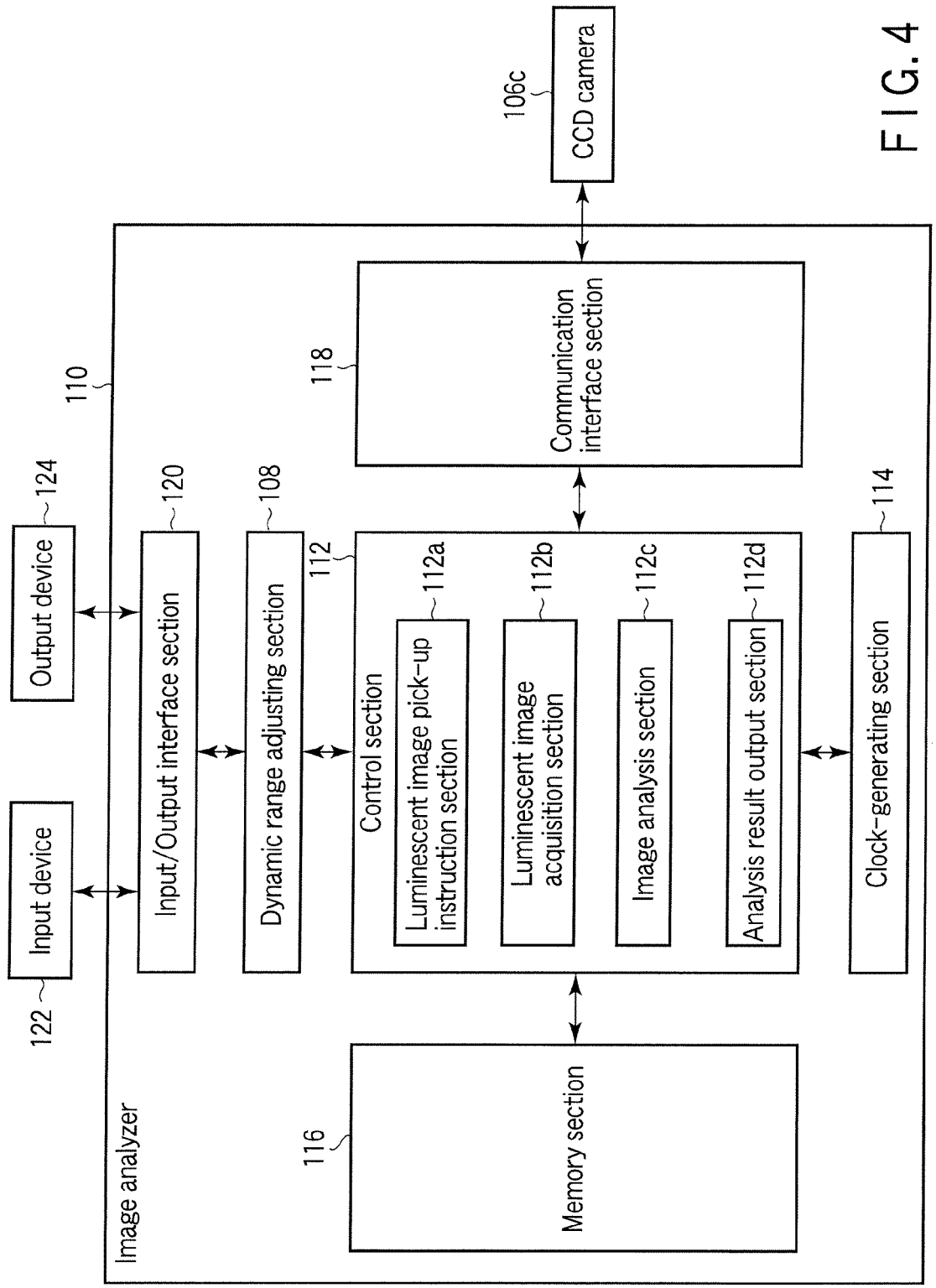
FIG. 4 is a block diagram illustrating one example of the construction of an image analyzer 110 of the observation system 100.

| Explanation of symbols | |
|---|---|
| 100 | Luminescence observation system |
| 103 | Vessel (Petri dish) |
| 104 | Stage |
| 106 | Luminescence image pick-up unit |

-continued

| Explanation of symbols | |
|---|---|
| 106a | Objective lens (for observing luminescence) |
| 106b | Dichroic mirror |
| 106c | CCD camera |
| 106d | Split image unit |
| 106e | Filter wheel |
| 106f | Imaging lens |
| 108 | Dynamic range adjusting section |
| 110 | Image analyzer |
| 112 | Control section |
| 112a | Luminescent image pick-up instruction section |
| 112b | Luminescent image acquisition section |
| 112c | Image analysis section |
| 112d | Analysis result output section |
| 114 | Clock-generating section |
| 116 | Memory section |
| 118 | Communication interface section |
| 120 | Input/Output interface section |
| 122 | Input apparatus |
| 124 | Output apparatus |

DETAILED DESCRIPTION OF THE INVENTION

Next, various embodiments of the luminescence measurement method and the luminescence measurement system according to the present invention will be explained in detail with reference to drawings. Incidentally, these embodiments are not intended to limit the scope of the present invention.

Especially, in the following embodiments, there may be explained cases where the present invention is applied to luminescent imaging. However, the present invention is not limited to such a luminescent imaging, but can be applied likewise to the measuring method using a luminometer, for instance.

First of all, the construction of a luminescence observation system (luminescence measuring system) 100 to be employed in the luminescence measurement method (specifically, a measuring step and an output step) according to the present invention will be explained with reference to FIG. 1, FIG. 2 and FIG. 3. FIG. 1 shows a diagram illustrating one example of the overall construction of luminescence observation system 100.

As shown in FIG. 1, the luminescence observation system 100 is constituted by a vessel 103 (specifically, it may be a Petri dish, a slide glass, a microplate, a gel-supporting member, a fine particle carrier, etc.) housing a biological sample 102, a stage 104 for mounting the vessel 103, a luminescence image pick-up unit 106, and an image analyzer 110. Herein, the luminescence observation system 100 may be constructed such that the luminescence image pick-up unit 106 for measuring a weak luminescence is disposed on the underside of the stage 104 so as to completely intercept the disturbing light from the direction above the sample on the occasion of opening or closing the cover, thereby making it possible to increase the S/N ratio of luminescent image. The luminescence image pick-up unit 106 may be formed of a laser scanning type optical system.

The biological sample 102 is formed of a living cell containing luminescence-associated protein that can be obtained by introducing a luminescence-associated gene into the protein. This biological sample 102 contains more than a prescribed quantity of a substance which is capable of reacting with the luminescence-associated protein. As for the luminescence-associated protein, it is selected from those exhibiting more than a prescribed level of Km value so as to make it possible to quantitatively determine the luminescence intensity in correspondence with the quantity of the substance. As for the object to be analyzed in this case, it may be a biological tissue including cells, or various kinds of internal organs or organ including such a biological tissue. Alternatively, the object to be analyzed may be an embryo or a bion having such a biological tissue, internal organ or organ. The stage 104 for sustaining the object to be analyzed may be designed in such a manner that specific cell(s) (one or more) to be analyzed would not be moved out of the visual field (preferably, the optical axis) for observing the luminescence of the object during a desired time period of analysis (for example, an object-fixing tool or a tracking mechanism for the stage).

The luminescence image pick-up unit 106 is, specifically, formed of an upright type luminescence microscope which is capable of picking up the luminescent image of the biological sample 102. As shown in FIG. 1, the luminescence image pick-up unit 106 is constituted by an objective lens 106a, a dichroic mirror 106b, a CCD camera 106c and an imaging lens 106f. The objective lens 106a is, specifically, constructed to have a value of (the number of apertures/magnification)$^2$ which is confined to 0.01 or more. The dichroic mirror 106b is employed for separating, color by color, the luminescence emitted from the biological sample 102, thereby measuring, color by color, the quantity of luminescence and the luminescence intensity by making use of the luminescence of two colors. The CCD camera 106c is used for taking the luminescent image and the brightfield image of the biological sample 102 that have been projected, through the objective lens 106a, the dichroic mirror 106b and the imaging lens 106f, on the chip surface of the CCD camera 106c. Further, the CCD camera 106c is connected with an image analyzer 110 to thereby enable it to communicate, through a wire or wireless circuit, with the image analyzer 110. In this case, if a plurality of biological samples 102 are existed within the range of picking up, the CCD camera 106c may be designed so as to perform the image pick-up of luminescence images and brightfield images of the plurality of biological samples 102. The imaging lens 106f is employed for picking up the image (specifically, an image including the biological sample 102) that has been entered, through the objective lens 106a and the dichroic mirror 106b, into the imaging lens 106f. Incidentally, in FIG. 1, there is illustrated one example wherein luminescent images each corresponding to a couple of beams separated by the dichroic mirror 106b are individually taken up by a couple of CCD cameras 106c. Therefore, in a case where only one beam is employed, the luminescence image pick-up unit 106 may be constituted by the objective lens 106a, a single CCD camera 106c and the imaging lens 106f.

When it is desired to measure the quantity of luminescence and the intensity of luminescence color by color by making use of two color beams, the luminescence image pick-up unit 106 may be constituted by the objective lens 106a, the CCD camera 106c, the split image unit 106d and the imaging lens 106f as shown in FIG. 2. Further, the CCD camera 106c may be used for taking the luminescent image (split image) and the brightfield image of the biological sample 102 that have been projected, through the split image unit 106d and the imaging lens 106f, on the chip surface of the CCD camera 106c. The split image unit 106d is used for separating beam emitted from the sample 102 color by color and for measuring the quantity of luminescence and the intensity of luminescence color by color by making use of two color beams.

Further, when it is desired to measure the quantity of luminescence and the intensity of luminescence color by color by making use of a plurality of color beams (namely, when a multi-color beam is employed), the luminescence image pick-up unit 106 may be constituted by the objective lens 106a, the CCD camera 106c, a filter wheel 106e and the imaging lens 106f as shown in FIG. 3. In this case, the CCD camera 106c may be used for taking the luminescent image and the brightfield image of the biological sample 102 that have been projected, through the filter wheel 106e and the imaging lens 106f, on the chip surface of the CCD camera 106c. The filter wheel 106e is used for separating beam emitted from the sample 102 color by color by way of filter exchange and for measuring the quantity of luminescence and the intensity of luminescence color by color by making use of a plurality of color beams.

Now turn back to FIG. 1, the image analyzer 110 is, specifically, formed of a personal computer. This image analyzer 110 is roughly constituted as shown in FIG. 4 by a control section 112, a clock-generating section 114 for measuring the time of the system, a memory section 116, a communication interface section 118, an input/output interface section 120, an input apparatus 122 and an output apparatus 124, wherein all of these sections are connected with each other through a bus. The details of these constructions shown in FIGS. 1 to 4 can be understood by referring to International Patent Publication WO2006/106882 (the title thereof: A method of measuring a quantity of luminescence at a prescribed site, An apparatus of measuring a quantity of luminescence at a prescribed site, A method of measuring a quantity of manifestation, and A measuring apparatus). Since this International Patent Publication discloses a method of analyzing two kinds of medical information on the same cell by making use of both of the fluorescent image and luminescent image thereof, the method can be also applied, as another embodiment of the present invention, to the method of analysis wherein a plural kinds of fluorescent marker substance differing in dynamic range (fluorescence-associated protein such as GFP, CFP, YFP, RFP, etc., for example) are employed. Further, in the case of BRET (bioluminescence resonance energy transfer), since it is an optical phenomenon wherein bioluminescence is combined with fluorescence, it is possible to obtain the advantage that a system for exciting fluorescence can be dispensed with. Furthermore, it is also possible to utilize, as fluorescence-associated protein, Oberlin, etc. other than luciferase.

The memory section 116 is formed of storage means, so that it may be, as a specific example, a memory device such as RAM, ROM, etc., a stationary disk device such as hard disk, a flexible disk, an optical disk, etc. This memory section 116 is designed to store data obtained by the processing of each of the sections of the control section 112. The communication interface section 118 acts to mediate the communication between the image analyzer 110 and the CCD camera 106a. Namely, the communication interface section 118 is provided with a function to communicate with other terminals so as to receive or send data through a wire or wireless communicating circuit. The input/output interface section 120 is connected with an input apparatus 122 and with an output apparatus 124. As for the output apparatus 124 in this case, it is possible to employ not only a monitor (including a home television) but also a speaker or a printer (incidentally, in the following description, the output apparatus 124 may be referred to as a monitor). Further, as for the input apparatus 122, it is possible to employ a key board, a mouse, a microphone as well as a monitor which is capable of functioning as a pointing device in cooperation with a mouse. In this case, based on a luminescent image displayed in a monitor employed as the output apparatus 124, an interested region including one or more of specific cells (or a cell group) to be analyzed within a desired time period of analysis or an interested site in a cell as well as measuring item(s) are designated through the input apparatus 122 by a user, thereby enabling the positional information (adress) of the region (or site) designated in the observing visual field to be stored in the memory section 116. Due to the information thus stored in this manner, it is now possible to perform image analysis which makes it possible to check up a plurality of regions (or sites) or temporally check up the specific cells (or a cell group) on the basis of time series.

Further, the image analyzer 110 is constructed in such a manner that when the kind (or the Km value itself) of luminescence-associated protein used as an object to be placed on the stage 104 is input through the input apparatus 122 by a user, the dynamic range of each of measuring item related to one of more of luminescence-associated protein to be used is specifically selected by a dynamic range adjusting section 108 from memory information that has been stored in advance such as a look-up table, thereby enabling a control mode corresponding to the collated dynamic range to be instructed to the control section 112. In this case, once the kind of luminescence-associated protein is specified, the kind of ground substance which causes the luminescence-associated protein to radiate can be univocally determined, so that the Km value to the ground substance may be also stored in advance in the look-up table. The control section 112 is designed such that each of processes (an imaging process, an image-obtaining process, a picture image processing for analysis and a process of analyzed results) according to the instructed control mode can be executed at each of the sections (a luminescent image pick-up instruction section 112a, a luminescent image acquisition section 112b, an image analysis section 112c and an analysis result output section 112d) while coordinating with the address of each of the designated regions (or sites) that have been stored in the memory section 118. Furthermore, the information related to the luminescent image and/or the analyzed results thus obtained is displayed on the picture plane of the output apparatus 124 after the information has been converted, through the dynamic range adjusting section 108, to an output format corresponding to the dynamic range. Incidentally, when it is desired to combine the information with a measuring item wherein luminescence-associated protein is employed, it is preferable to input the kind (or Km value itself) of the luminescence-associated protein. In this case however, since it is conceivable that, due to the modification of the luminescence-associated protein or fluorescence-associated protein, the Km value thereof may be varied from the Km value before the modification thereof, it is preferable to input the Km value of the protein to be actually used.

As for the instruction of picking up corresponding to the dynamic range and to be executed by the luminescent image pick-up instruction section 112a, it includes picking up intervals (for example, a video mode of not more than 5 seconds, a video mode consisting of intermediate intervals ranging from 6 seconds to 10 minutes, a time lapse mode consisting of long picking up intervals ranging from 11 minutes to 120 minutes, or a combination of these modes). As for the instruction of acquisition corresponding to the dynamic range and to be executed by the luminescent image acquisition section 112b, it includes for example the exposure time (a short time exposure mode of not more than one second, an intermediate exposure time exposure mode ranging from 2 seconds to 10 minutes and a long time exposure mode ranging from 6 minutes to 120 minutes) of an image pick-up device (for example, a CCD camera, a CMOS camera, etc.). At the image analysis section 112c, the analysis of each of the regions (or sites) related to the obtained luminescent image is executed based on such a computing algorithm that makes it possible to analyze each kind of measuring items in correspondence with the dynamic range. At the analysis result output section 112d also, the output of the output format (an image format, a numerical format, a graphic format, etc.) corresponding to each kinds of measuring items is executed. Finally, at the dynamic range adjusting section 108, the result of each kind of analyzed results that has been transmitted from the analysis result output section 112d is subjected to a conversion processing wherein the same or different output contents (image, numeral, graph, etc.) are converted based on a parameter (selected from the group consisting of color, color tone, gradation, brightness, dimension and video display speed) corresponding to the dynamic range before the result is displayed at the output apparatus 124. According to this system, a plural kinds of objects to be measured and varying in dynamic range or in Km value with respect to a substance to be measured and corresponding to measuring item can be applied to the same or different object to be analyzed. For example, a measuring item having a wide dynamic range such as ATP and a measuring item having a relatively narrow dynamic range such as a specific kind of gene expression may be applied to the same object to be analyzed, thereby realizing the advantage that each of the regions and/or site on the same picture image can be tracked concurrently and at real time. Although it is made possible to identify cells one by one as a luminescent image by superimposing the luminescent image with a bright visual field image which has been also obtained in this example, the luminescent image may not be superimposed with the bright visual field image, provided that the image pick-up device or luminescent reagent (luciferase, luciferin or other kinds of additives) is high in sensitivity. Further, as described hereinafter, depending on a purpose, even if various kinds of luminescent protein such as a glow type or flash type luminescent protein are prepared to thereby enable the same biological sample to be simultaneously labeled, it is possible to carry out the picking up and the analysis by means of the aforementioned system. Therefore, it is possible to realize a combination of assays or a multi-assay.

The control section 112 is provided with a control program such as OS (Operating System), a program regulating various kinds of procedures and an internal memory for storing data required, thereby making it possible to execute various kinds of processes based on these programs. This control section 112 is roughly constituted by the luminescent image pick-up instruction section 112a, the luminescent image acquisition section 112b, the image analysis section 112c and the analysis result output section 112d.

The luminescent image pick-up instruction section 112a is designed to instruct, through the communication interface section 118, the CCD camera 106c to execute the picking up of luminescent image and bright visual field image. The luminescent image acquisition section 112b is designed to receive, through the communication interface section 118, the luminescent image and the bright visual field image that have been taken by means of the CCD camera 106c. The control section 112 is designed to control the luminescent image pick-up instruction section 112a so as to execute repeated picking up of the luminescent image and the bright visual field image of biological sample 102.

In this case, on the occasion of performing the picking up of the luminescent image of biological sample 102 by means of the CCD camera 106c, a luminescence-associated protein having an appropriate Km value so as to prevent the generation of an extreme difference in luminescence intensity among the luminescence-associated proteins (for example, in a case where one of them is luciferase for quantitatively measure ATP and the other is luciferase for analyzing the gene expression) is selected (for example, luciferase having a higher Km value (Km>364 μM) as compared with the luciferase for analyzing the gene expression is selected as the luciferase for quantitatively measure ATP), thereby making it possible to concurrently perform the picking up in the same exposure time.

The image analysis section 112c is designed to quantitatively measure the luminescence intensity of each of luminescent colors on the basis of the luminescent image that has been obtained at the luminescent image acquisition section 112b. Further, the image analysis section 112c is designed to quantitatively measure fluctuation with time of the luminescence intensity of each of luminescent colors on the basis of a plurality of luminescent images that have been obtained at the luminescent image acquisition section 112b. The analysis result output section 112d is designed to feed the result of analysis obtained at the image analysis section 112c to the output apparatus 124. In this case, the analysis result output section 112d may be designed such that the time series data related to the luminescence intensity of each of luminescent colors that have been obtained at the image analysis section 112c are turned into a graph, which is then displayed at the output apparatus 124.

The above description illustrates one example of the construction of the luminescence observing system (luminescence measuring system) to be employed in the luminescence measuring method of the present invention. Incidentally, the output apparatus 124 may be designed such that a plurality of luminescent images corresponding to at least a portion of the time series numerical data can be fed in the form of video or parallel display to a monitor. As described above, according to the present invention, not only the kinetic analysis as to how the dynamics of a bioactive substance which is wide in dynamic range has been changed but also the analysis of the expression/fluctuation of a specific gene as to how the transcription of the specific gene related to the dynamics of the bioactive substance has been controlled can be performed quickly or at real-time on the same cell (or cell group). Therefore, it is possible to provide information accurately and quickly for use in the medical research or for clinical use (for example, response tests of drugs for the purpose of treatment, diagnosis and preventive medicine). Incidentally, in the case where a fluorescence image-taking unit is co-used in the analysis system for executing the method of the present invention, the fluorescence image-taking unit and the luminescent image pick-up unit may be placed on the same stage in such a manner that they are respectively disposed on a different optical axis or these units may be respectively constituted by a different apparatus (for example, a fluorescence microscope and a luminescence microscope) which is disposed on a different stage. Alternatively, these units may be designed to perform the picking up and the analysis while allowing a plurality of analyzing objects to successively move on the same or different stage. As for the analysis system, it can be applied also to a different kind of picking up system (various kinds of fiber scope (for example, an endoscope) and an image analysis type spectrometer (for example, a luminometer)) other than the aforementioned microscope-based system as long as the analysis system is equipped at least with the image analyzer as shown in FIG. 4. Further, in the case where the object is formed of a biological sample which has been isolated from a living body and incubated or artificially processed (cells, living tissue, internal organs (or organs), etc.), the analysis system should preferably be constructed in combination with a suitable culture apparatus so as to maintain the biological activity of the object during a prescribed period of analysis. However, when the object is an individual, the picking up can be intermittently performed while appropriately supplying or feeding oxygen and nutrition to the individual in place of the culture apparatus, thereby making it possible to execute the analysis in the same manner as described above.

EXAMPLE 1

(Enzymological Properties of Various Kinds of Luciferase and Application of Luciferase to Luminescence Measurement)

In this example 1, with a view to find out appropriate luciferase having a suitable Km value for the application of the present invention, the enzymological properties (Km value relative to D-luciferin and ATP) of luciferase available in the market (CBG, CBR, Eluc, Genji, GL3) were determined.

(Experiment Method 1: Calculation of Km Value of Various kind of Luciferase Relative to D-luciferin)

D-luciferin was added to a 0.1M ATP solution (Tris-HCl (pH=8.0)) to obtain various kinds of solutions differing in ultimate concentration of D-luciferin from each other, i.e. 5 μM, 10 μM, 20 μM, 40 μM, 80 μM, 160 μM, 320 μM, 640 μM, respectively, thus preparing 8 kinds of solutions. Then, a 100 μg/ml luciferase solution was prepared by making use of 0.1M Tris-HCl (pH=8.0).

Then, D-luciferin solutions having the aforementioned concentrations were respectively aliquoted to a vessel having 96 wells, thus creating wells each containing 50 μl of D-luciferin solution. Then, the luciferase solution was connected with a standard pump of luminometer, after which a program was prepared so as to initiate the measurement concurrent with the addition of 50 μl of the luciferase solution to each of the wells.

Subsequently, the program was started to measure the photon-count value at each D-luciferin concentration. Based on the results obtained, Lineweaver-Burk plot and Hanes-Woolf plot were prepared to determine the Km value of each of luciferase relative to D-luciferin. In this case, the Lineweaver-Burk plot can be represented by the following formula (1) and the Hanes-Woolf plot can be represented by the following formula (2).

Formula (1)

$$\frac{1}{v} = \frac{Km}{v_{max}} \times \frac{1}{[S]} + \frac{1}{v_{max}}$$ Formula (1)

Formula (2)

$$\frac{[S]}{v} = \frac{Km}{v_{max}} + \frac{[S]}{v_{max}}$$ Formula (2)

(Experiment Method 2: Calculation of Km Value of Various Kind of Luciferase Relative to ATP)

ATP was added to a 1 mM D-luciferin solution (Tris-HCl (pH-8.0)) to obtain various kinds of solutions differing in ultimate concentration of ATP from each other, i.e. 10 μM, 20 μM, 40 μM, 80 μM, 160 μM, 320 μM, 640 μM, 1280 μM, respectively, thus preparing 8 kinds of solutions differing in ATP concentration.

Then, a 100 μg/ml luciferase solution was prepared by making use of 0.1M Tris-HCl (pH-8.0). Subsequently, the ATP solutions each having the aforementioned concentration were respectively aliquoted to a vessel having 96 wells, thus creating wells each containing 50 μl of the ATP solution.

Then, the luciferase solution was connected with a standard pump of luminometer, after which a program was prepared so as to initiate the measurement concurrent with the addition of 50 μl of the luciferase solution to each of the wells.

Subsequently, the program was started to measure the photon-count value at each ATP concentration. Based on the results obtained, Lineweaver-Burk plot and Hanes-Woolf plot were prepared to determine the Km value of each kind of luciferase relative to ATP.

(Discussion)

FIG. 5 shows the Km values that have been determined from the results of above experiments. FIG. 5 is a table showing the Km value of each kind of luciferase relative to D-luciferin and ATP. Incidentally, in FIG. 5, the number described inside the parenthesis represents the Km value that was calculated by making use of the Hanes-Woolf plot and the number described outside the parenthesis represents the Km value that was calculated by making use of the Lineweaver-Burk plot.

Since the Km value of each kind of luciferase is treated in the same manner as Kd in general, it is conceivable that as the Km value becomes smaller, the affinity of luciferase to D-luciferin or ATP becomes higher. As shown in FIG. 5, the ranking of the affinity of luciferase to D-luciferin was confirmed as being CBG>ELuc>GL3>CBR>Genji.

When the facts that CBG, CBR and ELuc are respectively luciferase originating from Hikari Kometsuki and GL3 and Genji are respectively luciferase originating from firefly are taken into consideration, there will be recognized the trend that the affinity to D-luciferin becomes higher in the Luciferase originated from Hikari Kometsuki.

Further, with respect to the luminescence pattern obtained from the measurement using a luminometer also, the results obtained from the luciferase originated from Hikari Kometsuki were found different from the results obtained from the firefly-derived luciferase. Specifically, while the luciferase originated from Hikari Kometsuki exhibited a peak luminescence intensity 5 to 6 seconds after the addition of luciferin, the firefly-derived luciferase was confirmed to exhibit a peak luminescence intensity 0.5 to 1 second after the addition of luciferin.

As described above, since luciferase is likely to be classified into a flash type (requiring a short time for luminescence) and a glow type (requiring a long time for luminescence) depending on the species of organism representing the origin of luciferase, a desirable type of luciferase can be selected depending on the purpose of measurement or observation.

Further, there is a report describing that the difference of luminescence pattern as described above can be generated due to differences in amino acid residue of luciferase (R218, F250, G315, T343, etc.) existing in the vicinity of D-luciferin- or ATP-bonding site, these differences being caused by the point mutation of *P. pyralis* (see Bruce R. Branchini et al., Biochemistry, 2003, 42, pp. 10429-10436).

Since the aforementioned amino acid residue is known as being capable of contributing to the decay rate, it has been found possible to prepare the luciferase that is capable of exhibiting a luminescence pattern which differs from the flash type or the glow type by making use of genetic engineering techniques while taking the amino acid residue in each kind of luciferase into consideration.

Meanwhile, the ranking of the affinity of luciferase to ATP has been confirmed as being CBG>CBR, GL3>ELuc>Genji. Namely, the results thus obtained indicate that ELuc and Genji were relatively low in affinity to ATP as compared with that of other kinds of luciferase.

In this case, there is a possibility that since a small degree of variations in quantity of ATP cannot be fully reflected to the quantity of luminescence in the case of GL3 which is high in susceptibility, the luminescence intensity will be retained constant until the quantity of ATP is greatly attenuated. Specifically, in the experiments conducted by the present inventor, pGL3 was transfected to HeLa cell and, by making use of FCCP (carbonyl cyanide p-(trifluoromethoxy) phenylhydrazone) acting as an uncoupler, the production of ATP in mitochondria was suspended and then the luminescence intensity on this occasion was measured with time by making use of LUMINOVIEW (LV100) (trade name). However, the luminescence intensity was not attenuated even if the measurement was continued after the excitation thereof.

The cytoplasmic ATP of HeLa cell under the steady state is estimated as being 1.3 mM (see MV Zamaraeve et al., Cell Death and Differentiation, 2005, 12, pp. 1390-1397), so that if the luciferin-luciferase reaction is assumed as being abided by Michaelis-Menten equation, the reaction velocity of GL3 at this ATP concentration would be increased to about 85% of Vmax. Meanwhile, although it is reported that the concentration of cytoplasmic ATP after it was left to stand for 30 minutes after the treatment thereof with FCCP became about 50% of that of steady state (Takeshi Kubota et al., Biochimica et Biophysica Acta, 2005, 1744, pp. 19-28), the reaction velocity of GL3 in the reaction using 0.65 mM ATP is expected to be about 80% of Vmax. Namely, in the case of the measuring system using a cell wherein the quantity of manifestation of luciferase is caused to change, it is expected to be difficult to detect, by means of a CCD camera, the fluctuation of luminescence originating from a difference of 5% in reaction velocity as being the fluctuation in quantity of ATP.

Whereas, in the case of using the luciferase which is relatively low in affinity, the reaction velocity to be expected from Michaelis-Menten equation is slow, so that the same degree of difference in reaction velocity is caused to generate even when it is treated with drugs, thus making it possible to conclude that the aforementioned detection can be facilitated as compared with the case where GL3 is employed.

Namely, in the case of quantitatively measuring a substance existing at a ratio of more than a prescribed value in a biological sample such as ATP, it has been found possible to obtain a relatively large difference in reaction velocity and hence to facilitate the observation of a difference in luminescence intensity by suitably selecting a luminescence-associated material which is high in a Km value so as to prevent the concentration of the substance from approaching to the vicinity of Vmax in the Michaelis-Menten equation. On the occasion of measuring the ATP concentration inside a cell, it is preferable to estimate the quantity of ATP inside the cell and, based on this estimation, luciferase having an appropriate Km value may be selected. As described above, the low affinity (a high Km value) to ATP is an advantageous property on the occasion of measuring the ATP concentration inside a cell by making use of the luciferin-luciferase reaction.

The affinity to ATP in this case can be varied by means of the point mutation in the vicinity of ATP bonding site (see Bruce R. Branchini et al., Biochemistry, 2003, 42, pp. 10429-10436). Namely, an intracellular ATP-measuring system corresponding to many kinds of cells may be constructed by preparing a series of luciferase exhibiting various degrees of ATP affinity ranging from an intermediate affinity to a very low affinity (having Km values ranging from an intermediate Km value to a very high Km value). Incidentally, on the occasion of adjusting the ATP affinity by the introduction of a mutation into luciferase, it may be performed carefully so as to prevent the decrease of luminescence intensity.

The aforementioned method is directed, as an example, to an examination method wherein the luciferase which is low in affinity to a biological substance is used to measure or observe the substance for a long period of time when the substance is existed excessively in an organism. However, if the biological substance is existed only a very small quantity in an organism, the luciferase which is high in affinity to the substance may be selected. In this manner, the affinity to various kinds of biological substance existing in various degrees in an organism is respectively determined in advance and, based on the affinity thus determined, a suitable kind of luciferase is selected for any desired examination item, thereby making it possible to always perform the measurement or observation which is high in examination efficiency.

As explained above, as a result of extensive studies performed by the present inventor, it has been found out that it is possible to perform excellent measurement by selecting the luciferase which is low in affinity to a substance to be examined as the substance is existed excessively in an organism, especially a cell, as in the case of ATP. Especially, it has been found out as a result of the studies made on the affinity to ATP that it is possible to accurately measure quantitative fluctuation in an organism by selecting the luciferase having a Km value of not less than 364 μM, preferably not less than 500 μM. Further, when the Km value is adjusted through the modification of gene, it is possible to utilize also the luciferase which inherently exhibits a Km value falling out of the aforementioned range before the modification thereof. When the luciferase having such a Km value is utilized for luminously labeling a biological sample including a plurality of cells, it becomes possible, through the picking up of the luminescent picture image based on the luminescence of organism, to measure the luminescence intensity of each of the cells. Furthermore, it is possible to perform the analysis including the analysis of morphological fluctuation of each of cells on the basis of the luminescent image. Therefore, the measuring method of the present invention can be also provided as being useful in an application for accurately specifying the morphological fluctuation of each of cells such as shrinking that has been caused by the induction of apoptosis, etc. in conformity with the stimulation using a drug for example. In this case, the stimulation to be applied to an object to be analyzed may include physical energy such as electricity, light, magnetism, ultrasonic wave, etc. other than the addition or dosing of a chemical material such as a drug.

Namely, in the measurement of biological substance by making use of luciferase, the affinity to an object to be measured can be suitably combined with the affinity to a luminescent substrate, thereby making it possible to perform accurate quantitative measurement (especially, the measurement of fluctuation of concentration) under appropriate measuring conditions even if the object is enabled to excessively existed in an organism. This indicates in turn that the measuring method of the present invention is applicable to any desired examination for detecting very weak fluctuation in an organism or to any desired examination based on fluctuation in luminescence intensity of a substance which is capable of emitting a weak light such as a cell.

EXAMPLE 2

Comparison of Enzymological Properties Between Yaeyama Hime Firefly Originated Luciferase and Each of Other Kinds Luciferase Followings are explanation with regard to the enzymological properties of Yaeyama Hime firefly (scientific name: Luciola filiformis yayeyamana) originated luciferase which has been newly found and extracted by the present inventor and each of other kinds of luciferase described above and with regard to the application thereof.

As a background of this example, there has been a problem that since the luciferase available in the market is already modified by a genetic engineering method, it is difficult to expect any further technical progress. With a view to get out of this difficulty, the screening of novel luciferase was conducted by the present inventor. As a result, it was succeeded to obtain the luciferase gene (Sequence No. 1) originated from Yaeyama Hime firefly. Therefore, the determination of the enzymological properties of the luciferase of Yaeyama Hime firefly was performed. Namely, in this example, the determination of the enzymological properties (Km values thereof to D-luciferin and ATP) of the newly obtained luciferase originated from Yaeyama Hime firefly was performed. Further, for the purpose of comparison, the determination of the enzymological properties of various kinds of luciferase (CBG, CBR, ELuc, Genji, GL3) available from the market was concurrently executed.

From the sequence of gene, several kinds of firefly belonging to Luciola have been known to live in Japan. As a result of the following experiments conducted to Genji firefly (scientific name: Luciola cruciata, the name of luciferase will be referred to as Genji in the present specification), the gene arrangement thereof being already known, differences in Km value were found out. The present invention has taken notice of this differences in Km value and hence one of important subject matters of the present invention is to utilize the luciferase as a luminescent marker in conformity with purposes.

Experiment Method 1: Calculation of the Concentration of the Stock Solutions of D-luciferin and of ATP)

First of all, in order to calculate the concentration of D-luciferin, the ultraviolet/visible light absorption spectrum of D-luciferase was measured. In this measurement, the spectrum was measured using a diluted (by 4000 times) solution (in 0.1M Citrate/0.2M $Na_2HPO_4$ buffer, pH=5.0) of D-luciferin (Promega Co., Ltd.) stock solution (about 100 mM). As for the blank, the buffer described above was employed. FIG. 6 illustrates the ultraviolet/visible light absorption spectrum of D-luciferase.

By making use of the absorbency (328 nm, 0.467±0.006, n=10) obtained from the spectrum of FIG. 6, the concentration of the D-luciferin stock solution was calculated (D-luciferin: $\lambda_{max}$=328 nm, $\epsilon$c=18200, pH=5.0). As a result of the calculation, the concentration of the D-luciferin stock solution was found as being 102.6 mM.

Figure 7:
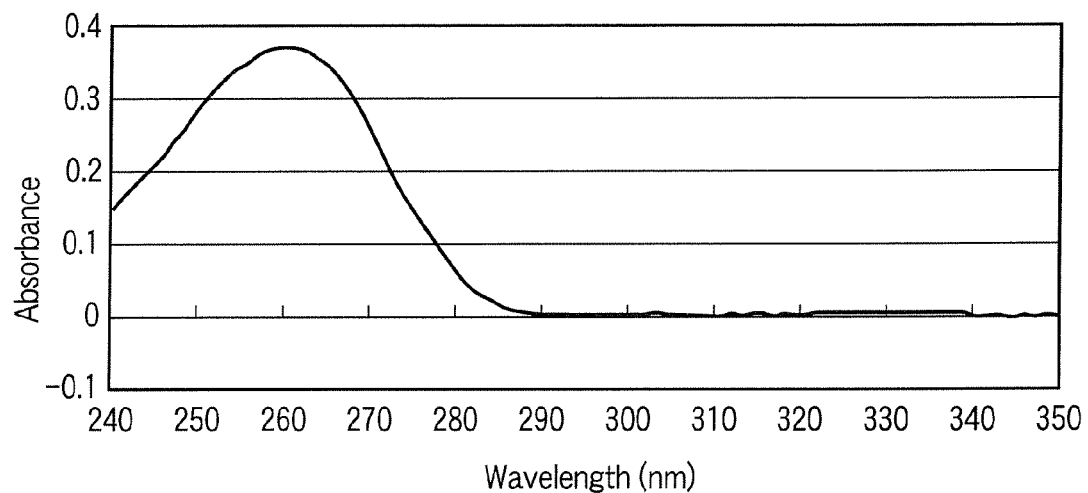
FIG. 7 is a graph showing the ultraviolet/visible light absorption spectrum of ATP.

Then, in order to calculate the concentration of ATP, the ultraviolet/visible light absorption spectrum of ATP was measured. In this measurement, the spectrum was measured using a diluted (by 2000 times) solution (in 0.1M Citrate/0.2M $Na_2HPO_4$ buffer, pH=7.0) of ATP stock solution (about 100 mM). As for the blank, the buffer described above was employed. FIG. 7 illustrates the ultraviolet/visible light absorption spectrum of ATP.

By making use of the absorbency (259 nm, 0.359±0.004, n=10) obtained from the spectrum of FIG. 7, the concentration of the ATP stock solution was calculated (ATP: $\lambda_{max}$=259 nm, $\epsilon$=15400, pH=7.0). As a result of the calculation, the concentration of the ATP stock solution was found as being 46.6 mM.

(Experiment Method 2: Purification of Various Kinds of Luciferase)

The purification of luciferase was performed according to the following procedure after establishing a luciferase-purification system utilizing affinity chromatography.

(Procedure of Transfection of Luciferase Expression Vector to Coli Bacillus)

First of all, 0.5 µL of luciferase expression vector was introduced into 50 µL of coli bacillus (JM109(DE3)). Then, the resultant liquid was subjected to a thermostatic treatment consisting of ice-cooling for 10 minutes, heating at 42° C. for one minute and ice-cooling for two minutes. Then, 2 µL of the resultant coli bacillus solution was added to 1 mL of an SOC culture medium.

Subsequently, the resultant solution of coli bacillus/SOC culture medium mixture was subjected to shaking at 37° C. for 20 minutes and to incubation. Then, 100 µL of the resultant solution was streaked onto an LB culture medium plate (Ampicillin 100 µg/mL+) and subjected to incubation overnight at 37° C.

(Purification of Luciferase by Means of Affinity Chromatography)

Then, the coli bacillus was fractured to obtain a raw extract, from which luciferase was purified by means of affinity chromatography.

Namely, first of all, a suspension of coli bacillus was subjected to centrifugal separation at 15000 rpm for 5 minutes to recover the pellets of coli bacillus, which was then suspended in 10 mL of TBS cooled to 4° C. Subsequently, by making use of French Pressure Cell, the fungus body was fractured. The resultant fungus body-fractured liquid was subjected to centrifugal separation (15000 rpm, 10 minutes) to remove settled residues and to recover a supernatant liquid.

Subsequently, 2 mL of TBS was added to a column having 2 mL of bed volume and subjected to filtration. Then, 500 µL of a Ni-Agar suspension and 2 mL of TBS were added to the column and the TBS was allowed to gravitationally drop (column equilibration). The supernatant liquid thus recovered was added to the column and allowed to gravitationally drop. Incidentally, the operation until the drop of the supernatant liquid was completed was performed inside a refrigerator at a temperature of 4° C.

Then, by making use of 1 mL of a 50 mM imidazole/TBS solution, the column was washed. Further, 2 mL of a 500 mM imidazole/TBS solution was added to the column to elute luciferase. The resultant elute was recovered in a 10 mL tube and immediately ice-cooled. Subsequently, the concentration of elute was performed by means of ultrafiltration.

Subsequently, the elute was moved 400 µL by 400 µL to a centrifugal concentration tube (SUPREC™-02, available from TaKaRa Co., Ltd. (exclusion limit molecular weight: 30,000)) and then subjected to centrifugal separation (5000 rpm, 30 minutes) until the elute was concentrated to about 100 µL. Thereafter, the absorbency of the concentrated elute was measured by means of a plate reader and the concentration of luciferase was calculated from the calibration curve which was prepared by making use of BSA. After finishing the calculation of concentration, the solution of luciferase was formulated as a 50% Glycerol solution and preserved at −20° C.

(Experiment Method 3: Calculation of Km Value of Various Kind of Luciferase Relative to D-luciferin)

First of all, a solution of 4 mM ATP and a solution of 8 mM MgSO$_4$ (in 0.1M Tris-HCl (pH-8.0)) were prepared. Then, D-luciferin was added to the ATP solution to obtain various kinds of solutions differing in ultimate concentration of D-luciferin from each other, i.e. 5 µM, 10 µM, 20 µM, 40 µM, 80 µM, 160 µM, 320 µM, 640 µM, respectively, thus preparing 8 kinds of solutions differing in concentration of D-luciferin from each other.

Then, a 100 µg/ml luciferase solution was prepared by making use of 0.1M Tris-HCl (pH-8.0) and D-luciferin solutions having the aforementioned concentrations were respectively aliquoted to a vessel having 96 wells, thus creating wells each containing 50 µl of D-luciferin solution.

Then, the luciferase solution was connected with a standard pump of luminometer, after which a program was prepared so as to initiate the measurement concurrent with the addition of 50 µl of the luciferase solution to each of the wells.

Subsequently, the program was started to measure the photon-count value at each D-luciferin concentration. Incidentally, the measurement was repeated five times at each concentration of D-luciferin.

Based on the results obtained, Lineweaver-Burk plot and Hanes-Woolf plot were prepared. In this case, the Lineweaver-Burk plot can be represented by the following formula (3) and the Hanes-Woolf plot can be represented by the following formula (4). Incidentally, the photon-count value immediately after the addition of an enzyme solution was defined as the initial velocity in the preparation of each of these plots.

Formula (3)

$$\frac{1}{v} = \frac{Km}{v_{max}} \times \frac{1}{[S]} + \frac{1}{v_{max}} \quad \text{Formula (3)}$$

Formula (4)

$$\frac{[S]}{v} = \frac{Km}{v_{max}} + \frac{[S]}{v_{max}} \quad \text{Formula (4)}$$

(V: Reaction velocity; $V_{MAX}$: Maximum velocity; [S]: Concentration of substrate; and Km: Michaelis constant)

Graphs illustrating the fluctuation of luminescence intensity of each kind of luciferase due to an increase in concentration of D-luciferin, the results of Lineweaver-Burk plot and the results of Hanes-Woolf plot are illustrated in FIGS. 8 to 25.

Figure 8:
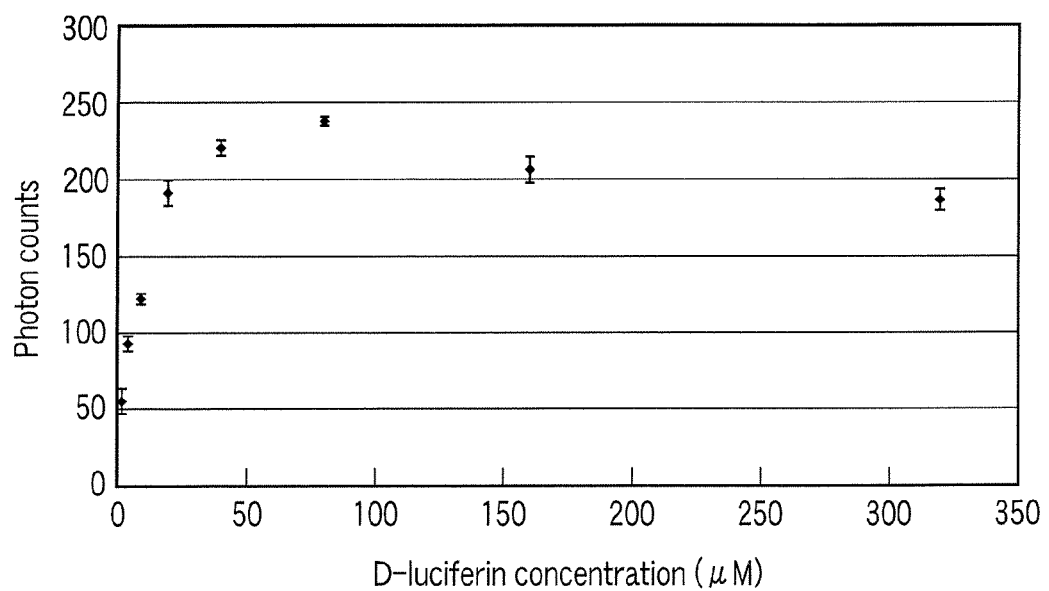
FIG. 8 is a graph showing the fluctuation of luminescence intensity due to an increase in concentration of D-luciferase of CBG.

Namely, FIG. 8 shows a graph illustrating the fluctuation of luminescence intensity due to an increase in concentration of D-luciferin in the case of CBG. FIG. 9 shows the Lineweaver-Burk plot, relative to the concentration of D-luciferin, of CBG. FIG. 10 shows the Hanes-Woolf plot, relative to the concentration of D-luciferin, of CBG.

As a result of these measurements, the Km value of CBG relative to D-luciferin as it was calculated from the Lineweaver-Burk plot was 10.5 µM and the Km value of CBG relative to D-luciferin as it was calculated from the Hanes-Woolf plot was 10.5 µM.

Further, in the case of CBR, the results were obtained as follows. Namely, FIG. 11 shows a graph illustrating the fluctuation of luminescence intensity due to an increase in concentration of D-luciferin in the case of CBR. FIG. 12 shows the Lineweaver-Burk plot, relative to the concentration of D-luciferin, of CBR. FIG. 13 shows the Hanes-Woolf plot, relative to the concentration of D-luciferin, of CBR.

As a result of these measurements, the Km value of CBR relative to D-luciferin as it was calculated from the Lineweaver-Burk plot was 36.4 µM and the Km value of CBR relative to D-luciferin as it was calculated from the Hanes-Woolf plot was 63.8 µM.

Further, in the case of ELuc, the results were obtained as follows. Namely, FIG. 14 shows a graph illustrating the fluctuation of luminescence intensity due to an increase in concentration of D-luciferin in the case of ELuc. FIG. 15 shows the Lineweaver-Burk plot, relative to the concentration of D-luciferin, of ELuc. FIG. 16 shows the Hanes-Woolf plot, relative to the concentration of D-luciferin, of ELuc.

As a result of these measurements, the Km value of ELuc relative to D-luciferin as it was calculated from the Lineweaver-Burk plot was 15.0 µM and the Km value of ELuc relative to D-luciferin as it was calculated from the Hanes-Woolf plot was 15.0 µM.

Further, in the case of Genji, the results were obtained as follows. Namely, FIG. 17 shows a graph illustrating the fluctuation of luminescence intensity due to an increase in concentration of D-luciferin in the case of Genji. FIG. 18 shows the Lineweaver-Burk plot, relative to the concentration of D-luciferin, of Genji. FIG. 19 shows the Hanes-Woolf plot, relative to the concentration of D-luciferin, of Genji, As a result of these measurements, the Km value of Genji relative to D-luciferin as it was calculated from the Lineweaver-Burk plot was 75.0 µM and the Km value of Genji relative to D-luciferin as it was calculated from the Hanes-Woolf plot was 75.0 µM.

Further, in the case of GL3, the results were obtained as follows. Namely, FIG. 20 shows a graph illustrating the fluctuation of luminescence intensity due to an increase in concentration of D-luciferin in the case of GL3. FIG. 21 shows the Lineweaver-Burk plot, relative to the concentration of D-luciferin, of GL3. FIG. 22 shows the Hanes-Woolf plot, relative to the concentration of D-luciferin, of GL3.

As a result of these measurements, the Km value of GL3 relative to D-luciferin as it was calculated from the Lineweaver-Burk plot was 33.3 µM and the Km value of GL3 relative to D-luciferin as it was calculated from the Hanes-Woolf plot was 25.0 µM.

Further, in the case of Yaeyama (luciferase originated from Yaeyama Hime firefly), the results were obtained as follows. Namely, FIG. 23 shows a graph illustrating the fluctuation of luminescence intensity due to an increase in concentration of D-luciferin in the case of Yaeyama. FIG. 24 shows the Lineweaver-Burk plot, relative to the concentration of D-luciferin, of Yaeyama. FIG. 25 shows the Hanes-Woolf plot, relative to the concentration of D-luciferin, of Yaeyama.

As a result of these measurements, the Km value of Yaeyama relative to D-luciferin as it was calculated from the Lineweaver-Burk plot was 100 µM and the Km value of Yaeyama relative to D-luciferin as it was calculated from the Hanes-Woolf plot was 100 µM.

(Experiment Method 4: Calculation of Km Value of Various Kind of Luciferase Relative to ATP)

In order to perform the calculation of Km value of each kind of the luciferase to ATP, an 8 mM $MgSO_4$ (in 0.1M Tris-HCl (pH=8.0)) solution of 1 mM D-luciferin was prepared at first.

Then, ATP was added to this D-luciferin to obtain various kinds of solutions differing in ultimate concentration of ATP from each other, i.e. 10 µM, 20 µM, 40 µM, 80 µM, 160 µM, 320 µM, 640 µM, 1280 µM, respectively, thus preparing 8 kinds of solutions differing in concentration of ATP from each other. Then, a 0.1M Tris-HCl (pH=8.0) solution of 100 µg/ml luciferase was prepared. The ATP solutions having the aforementioned concentrations were respectively aliquoted to a vessel having 96 wells, thus creating wells each containing 50 µl of the ATP solution.

Then, the luciferase solution was connected with a standard pump of luminometer, after which a program was prepared so as to initiate the measurement concurrent with the addition of 50 µl of the luciferase solution to each of the wells.

Subsequently, the program was started to measure the photon-count value at each ATP concentration. Incidentally, the measurement was repeated five times at each concentration of ATP.

Based on the results obtained, Lineweaver-Burk plot and Hanes-Woolf plot were prepared.

Graphs illustrating the fluctuation of luminescence intensity of each kind of luciferase due to an increase in concentration of ATP, the results of Lineweaver-Burk plot and the results of Hanes-Woolf plot are illustrated in FIGS. 26 to 43.

Namely, FIG. 26 shows a graph illustrating the fluctuation of luminescence intensity due to an increase in concentration of ATP in the case of CBG. FIG. 27 shows the Lineweaver-Burk plot, relative to the concentration of ATP, of CBG. FIG. 28 shows the Hanes-Woolf plot, relative to the concentration of ATP, of CBG.

As a result of these measurements, the Km value of CBG relative to ATP as it was calculated from the Lineweaver-Burk plot was 200 µM and the Km value of CBG relative to ATP as it was calculated from the Hanes-Woolf plot was 290 µM.

Figure 31:
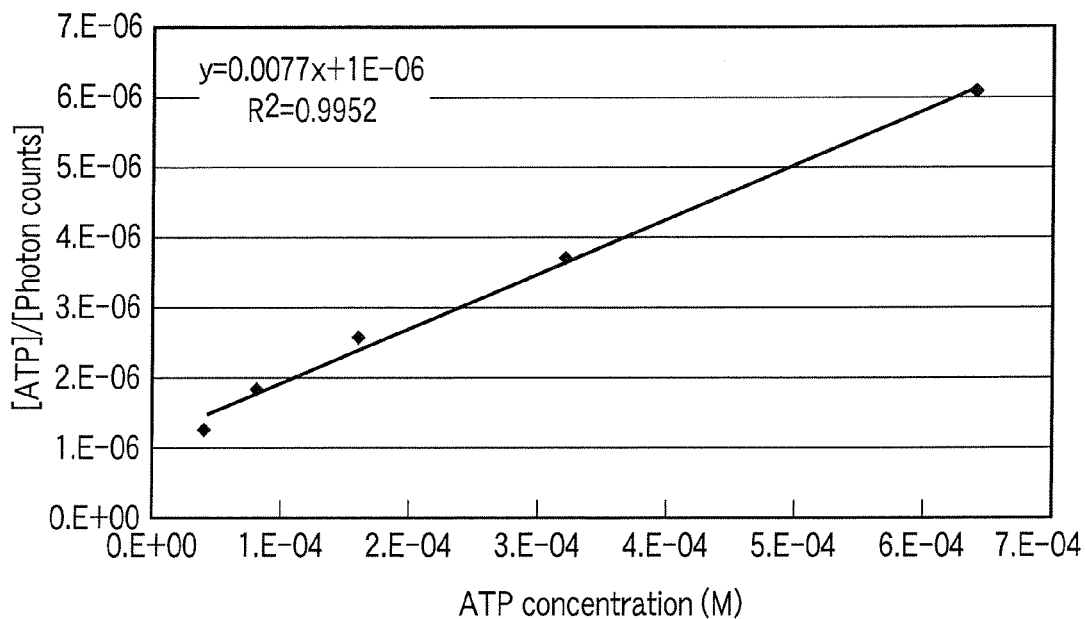
FIG. 31 is a graph showing Hanes-Woolf plots obtained relative to the concentration of ATP of CBR.

Further, in the case of CBR, the results were obtained as follows. Namely, FIG. 29 shows a graph illustrating the fluctuation of luminescence intensity due to an increase in concentration of ATP in the case of CBR. FIG. 30 shows the Lineweaver-Burk plot, relative to the concentration of ATP, of CBR. FIG. 31 shows the Hanes-Woolf plot, relative to the concentration of ATP, of CBR.

As a result of these measurements, the Km value of CBR relative to ATP as it was calculated from the Lineweaver-Burk plot was 110 µM and the Km value of CBR relative to ATP as it was calculated from the Hanes-Woolf plot was 130 µM.

Figure 32:
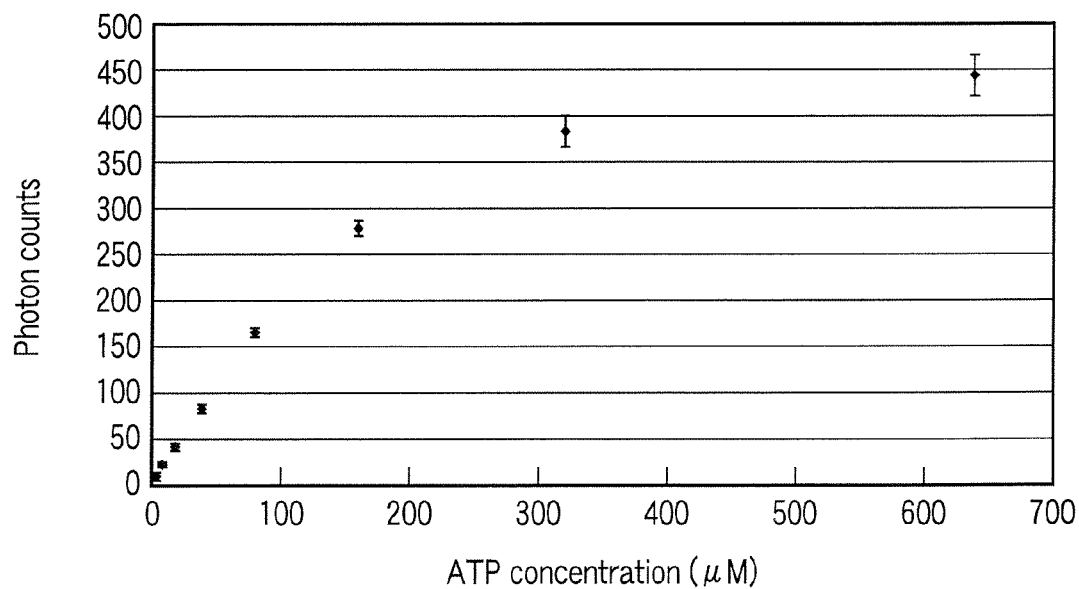
FIG. 32 is a graph showing fluctuation of luminescence intensity due to an increase in concentration of ATP of ELuc.
Figure 33:
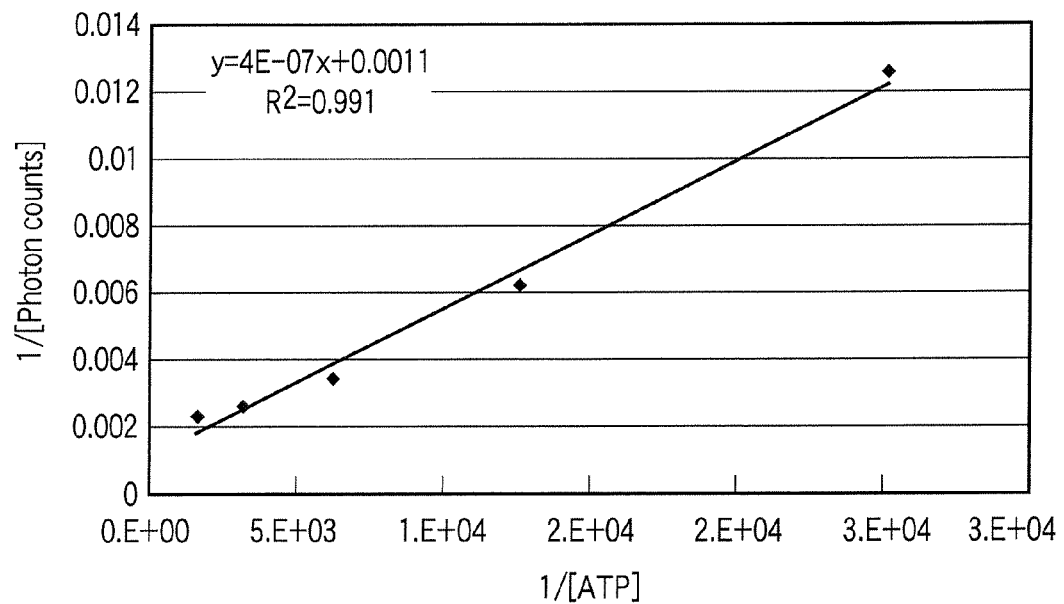
FIG. 33 is a graph showing Lineweaver-Burk plots obtained relative to the concentration of ATP of ELuc.
Figure 34:
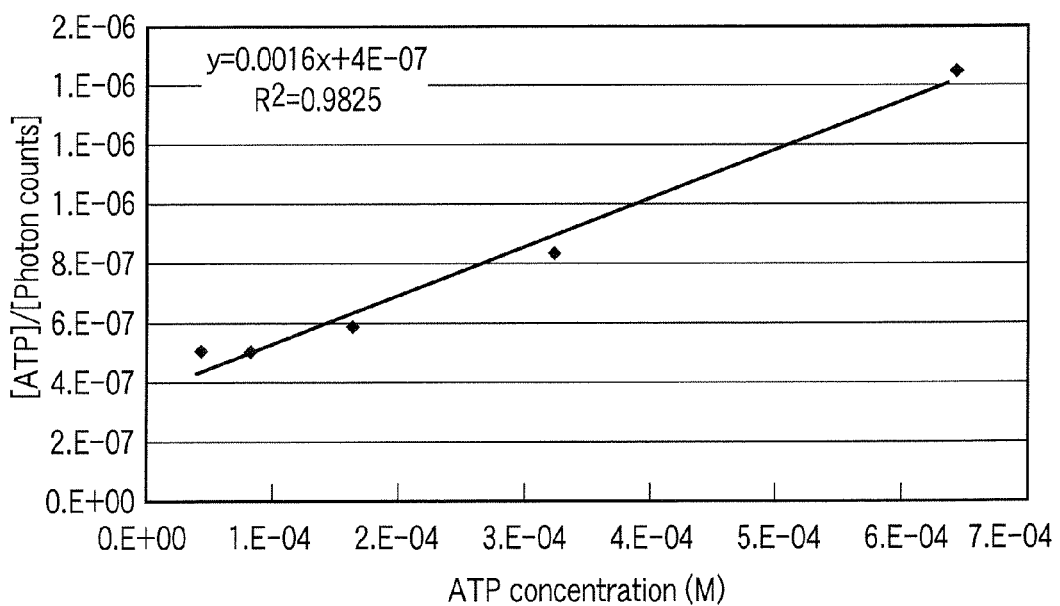
FIG. 34 is a graph showing Hanes-Woolf plots obtained relative to the concentration of ATP of ELuc.

Further, in the case of ELuc, the results were obtained as follows. Namely, FIG. 32 shows a graph illustrating the fluctuation of luminescence intensity due to an increase in concentration of ATP in the case of ELuc. FIG. 33 shows the Lineweaver-Burk plot, relative to the concentration of ATP, of ELuc. FIG. 34 shows the Hanes-Woolf plot, relative to the concentration of ATP, of ELuc.

As a result of these measurements, the Km value of ELuc relative to ATP as it was calculated from the Lineweaver-Burk plot was 364 µM and the Km value of ELuc relative to ATP as it was calculated from the Hanes-Woolf plot was 250 µM.

Figure 35:
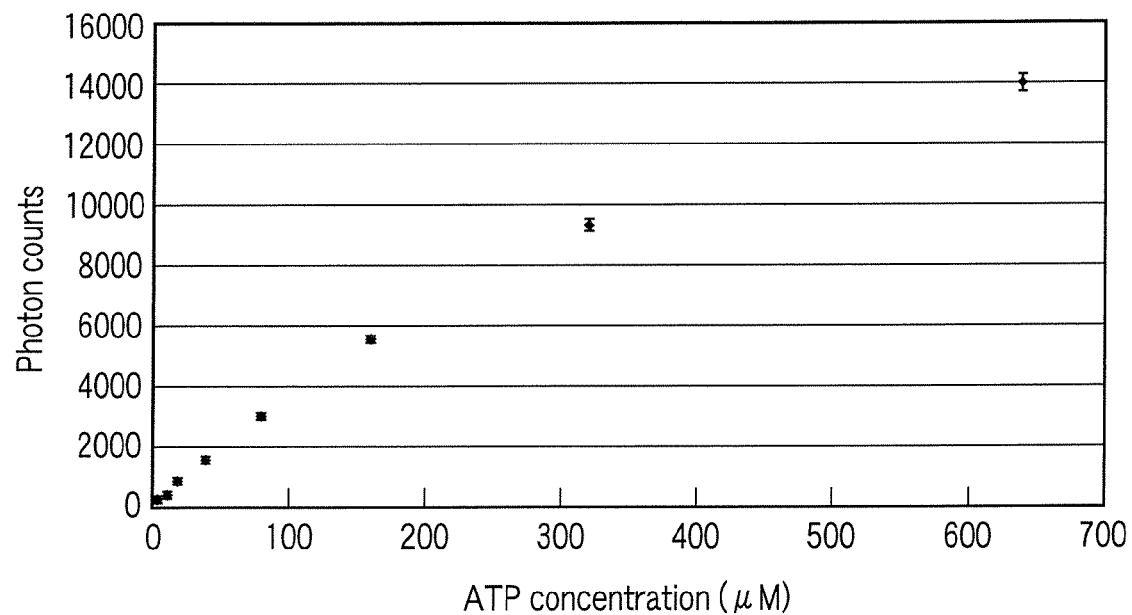
FIG. 35 is a graph showing the fluctuation of luminescence intensity due to an increase in concentration of ATP of Genji.
Figure 36:
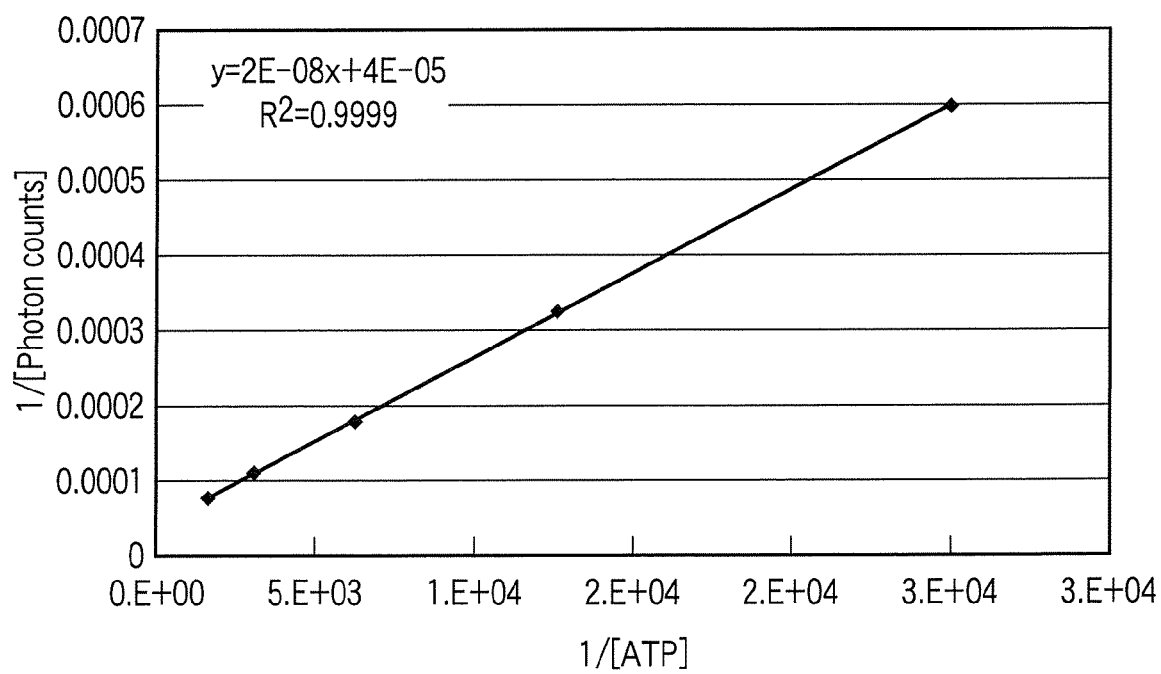
FIG. 36 is a graph showing Lineweaver-Burk plots obtained relative to the concentration of ATP of Genji.

Further, in the case of Genji, the results were obtained as follows. Namely, FIG. 35 shows a graph illustrating the fluctuation of luminescence intensity due to an increase in concentration of ATP in the case of Genji. FIG. 36 shows the Lineweaver-Burk plot, relative to the concentration of ATP, of Genji. FIG. 37 shows the Hanes-Woolf plot, relative to the concentration of ATP, of Genji.

As a result of these measurements, the Km value of Genji relative to ATP as it was calculated from the Lineweaver-Burk plot was 500 µM and the Km value of Genji relative to ATP as it was calculated from the Hanes-Woolf plot was 500 µM.

Further, in the case of GL3, the results were obtained as follows. Namely, FIG. 38 shows a graph illustrating the fluctuation of luminescence intensity due to an increase in concentration of ATP in the case of GL3. FIG. 39 shows the Lineweaver-Burk plot, relative to the concentration of ATP, of GL3. FIG. 40 shows the Hanes-Woolf plot, relative to the concentration of ATP, of GL3.

As a result of these measurements, the Km value of GL3 relative to ATP as it was calculated from the Lineweaver-Burk plot was 200 µM and the Km value of GL3 relative to ATP as it was calculated from the Hanes-Woolf plot was 200 µM.

Figures 43, 44:
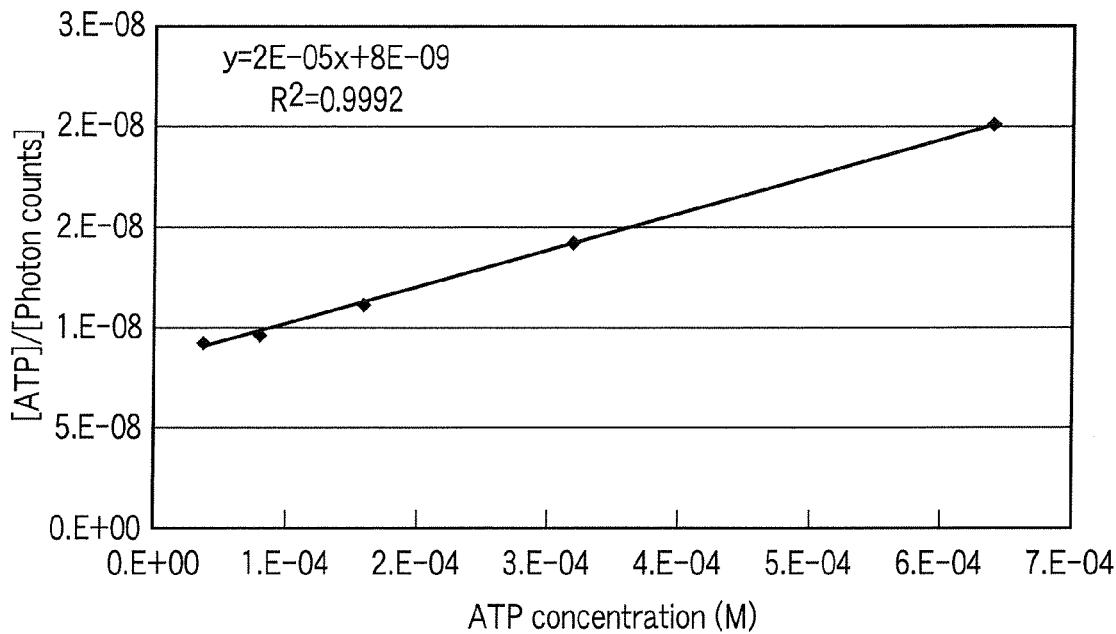
FIG. 43 is a graph showing Hanes-Woolf plots obtained relative to the concentration of ATP of Yaeyama.
FIG. 44 is a table illustrating the summary of the results wherein the Km values are calculated from the Lineweaver-Burk plots and the Hanes-Woolf plots created on the basis of the photon count values obtained by means of a luminometer.

Further, in the case of Yaeyama, the results were obtained as follows. Namely, FIG. 41 shows a graph illustrating the fluctuation of luminescence intensity due to an increase in concentration of ATP in the case of Yaeyama. FIG. 42 shows the Lineweaver-Burk plot, relative to the concentration of ATP, of Yaeyama. FIG. 43 shows the Hanes-Woolf plot, relative to the concentration of ATP, of Yaeyama.

As a result of these measurements, the Km value of Yaeyama relative to ATP as it was calculated from the Lineweaver-Burk plot was 400 µM and the Km value of Yaeyama relative to ATP as it was calculated from the Hanes-Woolf plot was 400 µM.

(Discussion)

The Lineweaver-Burk plot and the Hanes-Woolf plot were prepared from the photon count values obtained by the luminometer and, based on these plots, the Km values were calculated. FIG. 44 shows a summary of these results of calculation of the Km values. In FIG. 44, the number described inside the parenthesis represents the Km value that was calculated by making use of the Hanes-Woolf plot.

Since the Km value of each kind of luciferase is treated in the same manner as Kd in general, it is conceivable that as the Km value becomes smaller, the affinity of luciferase to D-luciferin or ATP becomes higher. Namely, the ranking of the affinity of luciferase to D-luciferin was confirmed as being CBG>ELuc>GL3>CBR>Genji>Yaeyama.

When the facts that CBG, CBR and ELuc are respectively luciferase originating from Hikari Kometsuki and GL3, Genji and Yaeyama are respectively luciferase originating from firefly are taken into consideration, there will be recognized the trend that the affinity to D-luciferin becomes higher in the Luciferase originated from Hikari Kometsuki.

Although data are not shown herein, the results obtained from the Luciferase originated from Hikari Kometsuki were found different from the results obtained from the firefly-derived luciferase with respect also to the luminescence pattern obtained from the measurement using a luminometer. Specifically, while the Luciferase originated from Hikari Kometsuki exhibited a peak luminescence intensity 5 to 6 seconds after the addition of luciferin, i.e. so-called glow type luminescence, the firefly-derived luciferase was confirmed to exhibit a peak luminescence intensity 0.5 to 1 second after the addition of luciferin, i.e. so-called flash type luminescence. With respect to the Luciferase originated from Yaeyama which was obtained by the present inventor at this time, since it exhibited a peak luminescence intensity 0.5 to 1 second after the addition of luciferin, this Luciferase was confirmed as being of flash type.

Further, there is a report describing that the difference of luminescence pattern as described above can be generated due to differences in amino acid residue of luciferase (R218, F250, G315, T343, etc.) existing in the vicinity of D-luciferin- or ATP-bonding site, these differences being caused by the point mutation of *P. pyralis* (see Bruce R. Branchini et al., Biochemistry, 2003, 42, pp. 10429-10436).

Since the aforementioned amino acid residue is known as being capable of contributing to the decay rate, it has been found possible to prepare the luciferase that is capable of exhibiting a luminescence pattern which differs from the flash type or the glow type by making use of genetic engineering techniques while taking the amino acid residue in each kind of luciferase into consideration.

Meanwhile, the ranking of the affinity of luciferase to ATP has been confirmed as being CBG>CBR, GL3>ELuc>Yaeyama>Genji. Namely, the results thus obtained indicate that, although it is inferior as compared with Genji, Yaeyama was relatively low in affinity to ATP as compared with that of other kinds of luciferase. This low affinity to ATP is an advantageous property on the occasion of quantitatively determining the intercellular ATP concentration by making use of the luciferin-luciferase reaction.

In this case, there is a possibility that since a small degree of variations in quantity of ATP cannot be fully reflected to the quantity of luminescence in the case of GL3 which is high in susceptibility, the luminescence intensity will be retained constant until the quantity of ATP is greatly attenuated. Specifically, in the experiments conducted by the present inventor, pGL3 was transfected to HeLa cell and, by making use of FCCP acting as an uncoupler, the production of ATP in mitochondria was suspended and then the luminescence intensity on this occasion was measured with time by making use of LUMINOVIEW (LV100) (trade name). However, the luminescence intensity was not attenuated even if the measurement was continued after the excitation thereof.

The cytoplasmic ATP of HeLa cell under the steady state is estimated as being 1.3 mM (see MV Zamaraeve et al., Cell Death and Differentiation, 2005, 12, pp. 1390-1397), so that if the luciferin-luciferase reaction is assumed as being abided by Michaelis-Menten equation, the reaction velocity of GL3 at this ATP concentration would be increased to about 85% of Vmax. Meanwhile, although it is reported that the concentration of cytoplasmic ATP after it was left to stand for 30 minutes after the treatment thereof with FCCP became about 50% of that of steady state (see Takeshi Kubota et al., Biochimica et Biophysica Acta, 2005, 1744, pp. 19-28), the reaction velocity of GL3 in the reaction using 0.65 mM ATP is expected to be about 80% of Vmax. Therefore, in the case of the measuring system using a cell wherein the quantity of manifestation of luciferase is caused to change, it is expected to be difficult to detect, by means of a CCD camera, the fluctuation of luminescence originating from a difference of 5% in reaction velocity as being the fluctuation in quantity of ATP.

Meanwhile, in the case of using Yaeyama, a reaction velocity corresponding to about 80% of Vmax in the case of 1.35 mM ATP and a reaction velocity corresponding to about 60% of Vmax in the case of 0.65 mM ATP are expected to be realized in view of the Michaelis-Menten equation, so that a difference of 20% in reaction velocity would be caused to generate as it is treated with drugs (FCCP treatment), thus finding that the detection can be facilitated as compared with the case where GL3 is employed. Namely, Yaeyama is found capable of exhibiting the most advantageous Km value in the luminescence imaging method of ATP. Further, when the above-described examples of GL3 and Yaeyama are taken into account, it is preferable to select the luciferase after estimating the quantity of ATP inside the cell on the occasion of measuring the intercellular ATP concentration.

The affinity to ATP in this case can be varied by means of the point mutation in the vicinity of ATP bonding site (see Bruce R. Branchini et al., Biochemistry, 2003, 42, pp. 10429-10436). Namely, by preparing a series of luciferase exhibiting various degrees of ATP affinity ranging from an intermediate affinity to a very low affinity (having Km values ranging from an intermediate Km value to a very high Km value), an intracellular ATP-measuring system corresponding to many kinds of cells can be constructed. Incidentally, since it is known that the luminescence intensity is caused to decrease in the case of the luciferase which has been modified through the introduction of mutation, the Yaeyama may be modified so as to adjust the ATP affinity while taking into consideration the retention of high luminescence intensity.

EXAMPLE 3

In this example 3, the object of experiment was directed to a plurality of HeLa cells having a luciferase gene introduced therein. By making use of luminometer (Chronos, ATTO Co., Ltd.), the luminescence of the HeLa cells to be induced by drug stimulation was tracked with time and the results obtained were compared with the quantity of fluctuation in luminescence that had been brought about by the luciferase gene.

A drug Staurosporine (STS) is known as being capable of obstructing PKC and of inducing apoptosis. Further, it is reported that once apoptosis has been induced by the STS, the intercellular ATP concentration is caused to increase at the initial stage of apoptosis (see MV Zamaraeva et al., Cell Death and Differentiation (2005), 12, pp. 1390-1397). In this example, the increase of the intercellular ATP concentration on the occasion of the induction of apoptosis into the HeLa cells by making use of the STS was detected by the increase of luminescence to be brought about by the ELuc and GL3, and the results obtained were compared with each other.

(Procedures of Experiment)

(1) A SV40 promoter/Emerald Luc expressing vector (Tohyobou Co., Ltd.) and a SV40 promotor/GL3 expressing vector were respectively introduced into HeLa cells which had been seeded in a glass bottom dish, thereby preparing the HeLa cells which were capable of constantly expressing luciferase.

(2) D-luciferin was added to the above-described samples to obtain the samples containing D-luciferin at an ultimate concentration of 0.5 mM. The resultant samples were left to stand for one hour in an incubator.

(3) The samples were set in a luminometer and then Staurosporine (STS) was added to these samples so as to make the ultimate concentration into 4 μM.

(4) After the addition of the drug, the measurement using the luminometer was initiated and fluctuation in luminescence after the stimulation using the drug were tracked with time.

Figure 45:
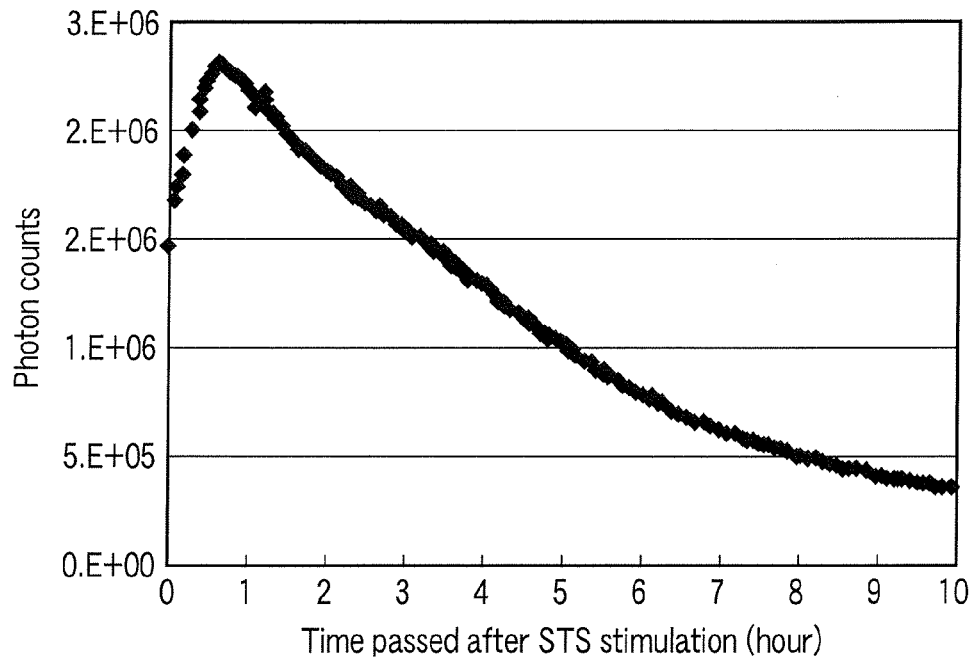
FIG. 45 is a graph showing the fluctuation of luminescence of ELuc obtained on the basis of the quantity of ATP in cells measured using a luminometer (Chronos)
Figure 46:
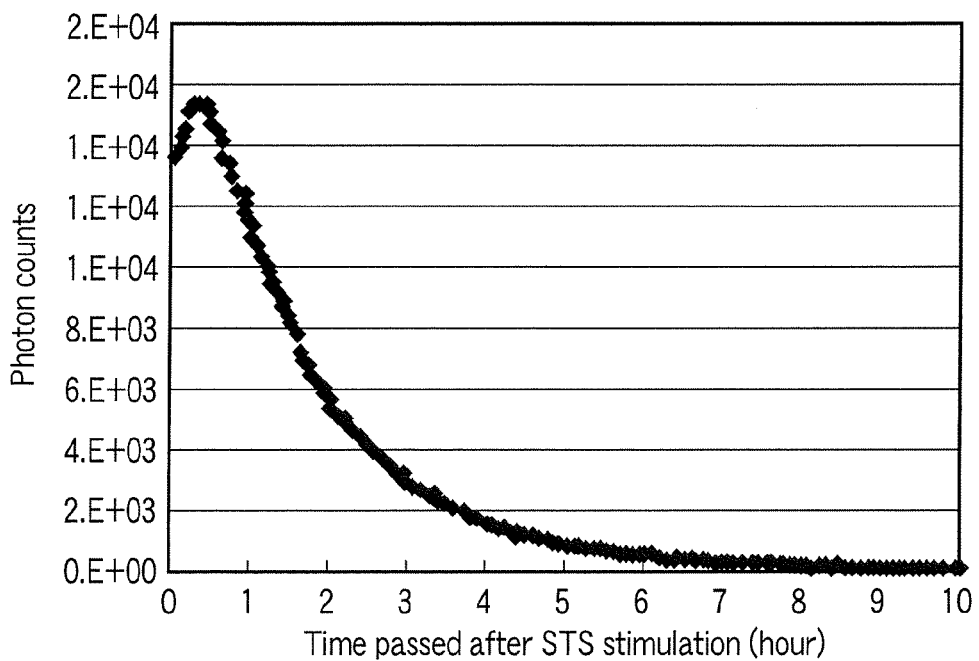
FIG. 46 is a graph showing the fluctuation of luminescence of GL3 obtained on the basis of the quantity of ATP in cells measured using a luminometer (Chronos)

As a result, fluctuation in luminescence intensity after the stimulation with STS were obtained as shown in FIG. 45 and FIG. 46. In this case, FIG. 45 is a graph showing the fluctuation of luminescence of ELuc obtained in the measurement of the quantity of intercellular ATP measured using a luminometer (Chronos) and FIG. 46 is a graph showing the fluctuation of luminescence of GL3 obtained in the measurement of the quantity of intercellular ATP measured using a luminometer (Chronos). This experiment was performed under the conditions wherein OPTI-MEM and 0.5 mM D-luciferin were used in the measurement using Chronos (ATTO Co., Ltd.) (36° C., 10-second integration data). After the stimulation using 4 μM Staurosporine (STS), the measurement was started.

As shown in FIG. 45 and FIG. 46, it will be recognized through the comparison between the fluctuation of luminescence of ELuc and GL3 that ELuc was more preferable in increasing the magnitude of fluctuation, thereby facilitating the detection using a luminometer. These results indicate that the employment of luciferase exhibiting a lower affinity to ATP is advantageous in the measurement of the fluctuation of ATP.

EXAMPLE 4

In this example 4, the object of experiment was directed to a plurality of HeLa cells having a luciferase gene introduced therein. By making use of LV200 (Olympus Co., Ltd.) representing a luminescence imaging system which was capable of executing the picking up/observation of three kinds of images, i.e. a fluorescent-transmitting image, a luminescent (chemical luminescence and/or biological luminescence) image and a transmitting bright visual field image, the luminescence of specific HeLa cells to be induced by drug stimulation was tracked with time and the luminescence intensity thereof was tracked. This luminescence imaging system was equipped with a component which was capable of cultivating a sample including cells, with a common pick up component (an objective lens, an imaging lens and a CCD camera), and an illumination system which was capable of executing the irradiation for exciting fluorescence and illumination of bright visual field. It is possible, with this system, to selectively obtaining an image from these three kinds of image and to individually display or analyze each of these images in accordance with the instruction of an operator. Therefore, it is possible for an operator to optionally give instructions through an interface of the system or to output the results of the analysis of these images.

(Procedures of Experiment)

(1) A SV40 promoter/Emerald Luc expressing vector (Tohyobou Co., Ltd.) was introduced into HeLa cells which had been seeded in a glass bottom dish, thereby preparing the HeLa cells which were capable of constantly expressing luciferase.

(2) D-luciferin was added to the above-described samples to obtain the samples containing D-luciferin at an ultimate concentration of 0.5 mM. The resultant samples were left to stand for one hour in an incubator.

(3) The samples were set in a luminescence imaging apparatus and then Staurosporine (STS) was added to these samples so as to make the ultimate concentration into 4 μM.

(4) After the addition of the drug, the measurement using the luminometer was initiated and fluctuation in luminescence after the stimulation using the drug were tracked with time.

Figure 48:
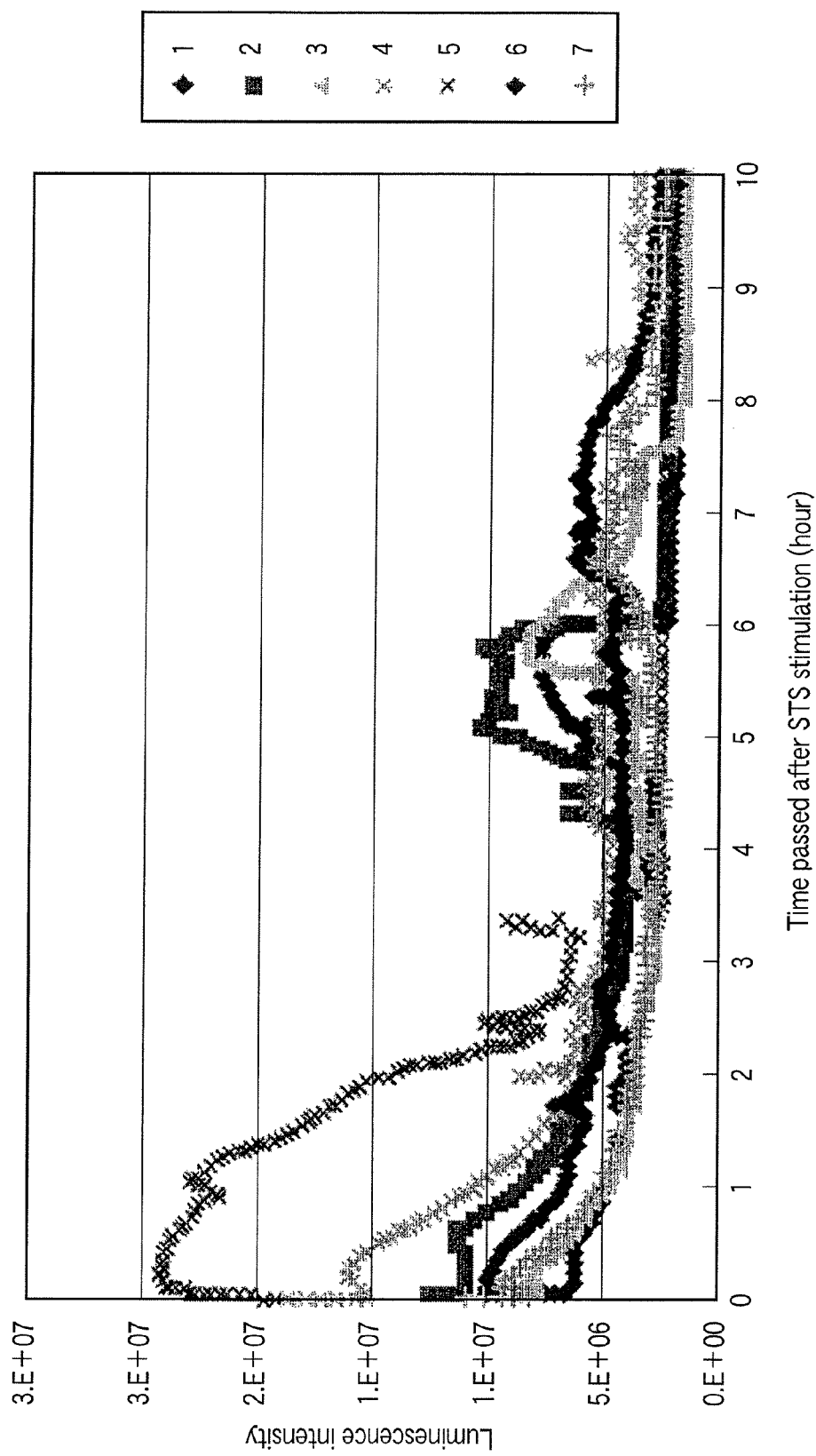
FIG. 48 is a graph showing the fluctuation of luminescence intensity after the STS stimulation in each of cells (ELuc expressing HeLa cells: 1-7) that has been analyzed from the images (1-7) each rectangularly encircled in FIG. 47.

As a result, it was possible to observe the luminescent image and the fluctuation in luminescence intensity as shown in FIG. 47 and FIG. 48. In this case, FIG. 47 is a graph showing a luminescent image in an ELuc expressing HeLa cell which was obtained immediately after the drug stimulation. The conditions for this experiment were as follows. By making use of 0.5 mM D-luciferin/OPTI-MEM, the measurement of ELuc control vector-introduced HeLa cell (seeded in a glass bottom dish) was performed using LV200 (Olympus Co., Ltd.). As for the CCD camera, an ImagEM was used. The picking up was performed under the conditions of: EM-Gain 200, binning 1×1, 10 sec exposure, 15 sec intervals, 40× objective lens. The measurement was started after the stimulation using 4 μM Staurosporine (STS). FIG. 48 is a graph showing the fluctuation of luminescence intensity after the STS stimulation in each of cells (ELuc expressing HeLa cells: 1 to 7) that has been analyzed from the images (1 to 7) each rectangularly encircled in FIG. 47.

As shown in FIG. 48, it has been found possible to track with time the luminescence of a specific HeLa cell by means of luminescent imaging and by making use of the luciferase which is low in affinity to ATP. Further, herein, FIG. 49 shows one example illustrating a luminescence image which was photographed prior to the stimulation of cell (prior to the induction of apoptosis by the stimulation of cell) according to the experiment procedures and under the experimental conditions described above. Further, FIG. 50 shows images which are designated as three measuring regions (ROI: regions of interest) in the luminescent image shown FIG. 49.

Figure 51:
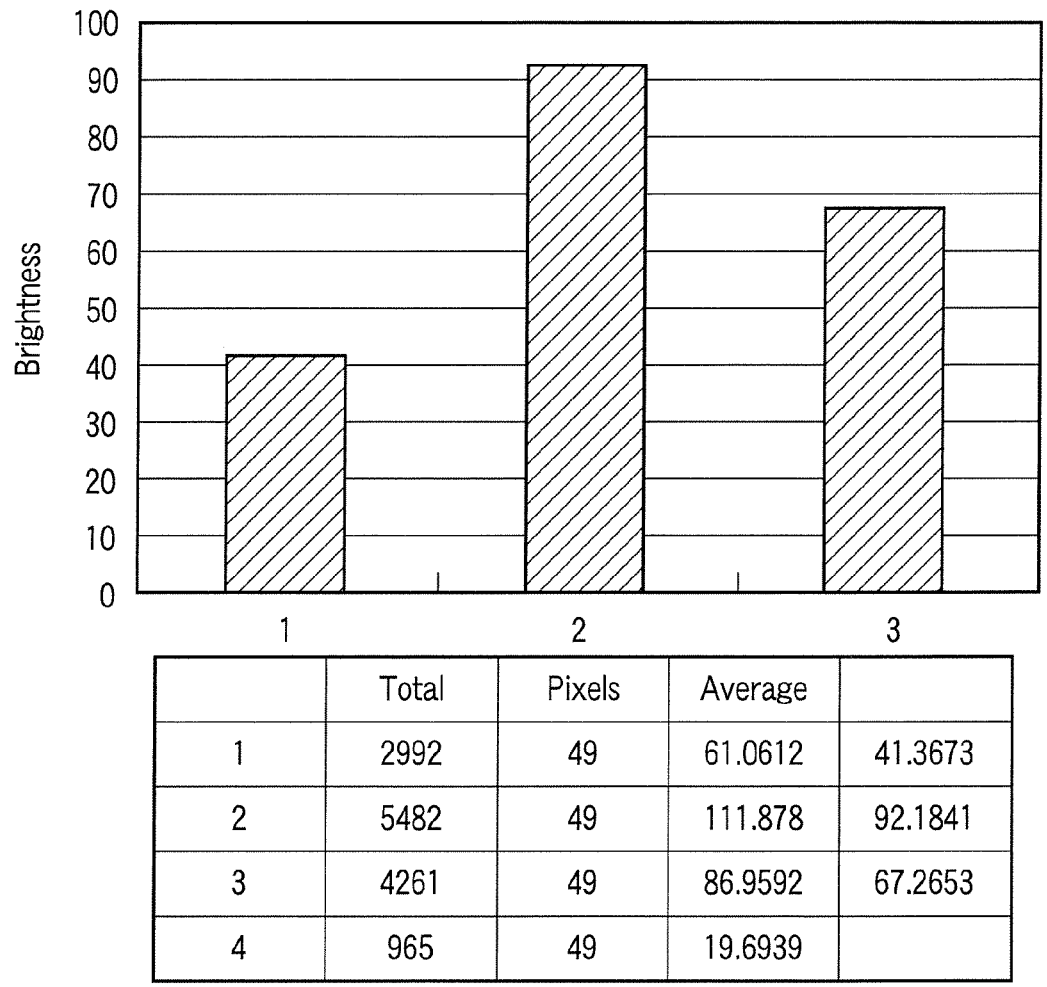
FIG. 51 is a graph showing the brightness of luminescence in three measurement regions and a table thereof.

As shown in FIG. 49, according to the experiment procedures and under the experimental conditions described above, it was possible to obtain a luminescent image (magnification: 100 times) related to a single cell. In this luminescent image, three cells are photographed. Among these cells, the cell located at the center is photographed in such a manner that the upper portion thereof is the brightest, the lower portion thereof is the next in brightness to the upper portion, and the intermediate portion thereof is somewhat dark. Then, as shown in FIG. 50, Three measuring regions (ROI) were designated from the luminescent image of FIG. 49 and the brightness of luminescence of each pixel group (49 pixels) in three regions was measured. Herein, FIG. 51 shows the values of luminescent brightness in three regions and the graph thereof. Incidentally, the values of luminescent brightness are represented by an arbitrary unit, so that the numbers "1", "2" and "3" in the lower table of FIG. 51 represent designated three measuring regions and the number "4" represents the background (an optional designated region containing no cell in the image). Further, "Total" in the table represents a total of the values of luminescent brightness in 49 pixels. "Average" in the table represents an average of the values of luminescent brightness of unit pixel. The graph of FIG. 50 illustrates the results obtained by correcting the average of the values of luminescent brightness with an average (=19.6939) of the values of luminescent brightness of the background.

When the ATP is consumed in a state where cells are still alive, the luminescence to be derived therefrom would become dark. Therefore, in the region where biological metabolic activity is weak in the same cell, the ATP can be hardly consumed, resulting in the generation of bright luminescence. As shown in FIG. 50, it has been found possible to quantitatively perform comparative analysis by executing only one picking up of the distribution of substance (ATP) to be measured, the distribution extending from a high concentration to a low concentration. When a tracking experiment was performed after the stimulation of the same cell, the brightness was gradually increased in every designated regions, thus indicating the deterioration of biological metabolic activity. Further, it was also confirmed that as the designated region became darker, the luminescence could be more quickly turned into higher brightness. As described above, according to this example 4, the distribution of the substance to be measured can be quantified among a plurality of cells or in each of the regions within the same cell, thereby making it possible to track the luminescence with time. In view of these results, it is possible, according to the luminescence measuring method of the present invention, to realize the execution of luminescence analysis of each of emitting sites exhibiting a wide dynamic range in an object to be analyzed (for example, a biological tissue or a cultivated cell group (or a segment of various internal organs)) which is positioned within the visual field of observation. Therefore, it is possible to execute, while minimizing the damage to an organism, the quantitative kinetic analysis of a plurality of sites in a single object to be analyzed and/or each of a plurality of objects to be analyzed with respect to biological active substances each exhibiting diverse dynamic range (for example, ATP, calcium ion, cAMP). Further, since the dynamic range can be altered in conformity with the Km value, it is possible to execute quantitative measurement in conformity with the quantity of substance and to adjust the luminescence intensity so as to prevent the generation of an extreme difference in luminescence intensity. As a result, it is possible to concurrently perform the tests of various items by making use of the same weak-light detecting apparatus.

As described above, the luminescence measuring method and the luminescence measuring system according to the present invention can be suitably applied to various fields such as a biological field, a pharmaceutical field, a medical field, etc.

What is claimed is:

1. A luminescence measurement system for executing a luminescence measuring method for measuring luminescence emitted from a biological sample, the system comprising:
    an image obtainer for obtaining a luminescent image from the biological sample;
    an image analysis section for executing image processing for analyzing the luminescent image obtained from the image obtainer;
    an output device for outputting a result of the analysis of image obtained from the image analysis section; and
    a dynamic range adjusting section for adjusting the image obtainer, the image analysis section in conformity with the Km value of a luminescent protein in the biological sample, wherein the biological sample has one or more regions and the image analysis section analyzes each of the one or more regions based on a dynamic range for each of the one or more regions independently.

2. The luminescence measurement system according to claim 1, wherein the dynamic range adjusting section is provided with a plurality of control modes.

3. The luminescence measurement system according to claim 1, which further comprises:
    an input device for designating a desired region and/or a desired site in the biological sample; and
    a memory section for storing information input from the input device; wherein
    the dynamic range adjusting section is designed to output an output content in which an image and an analyzed image are formulated in conformity with the information stored in the memory section.

4. The luminescence measurement system according to claim 1, wherein the dynamic range adjusting section is configured to display, through the output device, an analysis result that has been obtained by the image analysis section and converted through image obtainer and the dynamic range adjusting section based on a parameter corresponding to the dynamic range.

5. The luminescence measurement system according to claim 1, wherein the biological sample has two or more regions and the dynamic range adjusting section analyzes each of two one or more regions based on a dynamic range for each of the two or more regions.

* * * * *

SEQUENCE LISTING

```
<160> NUMBER OF SEQ ID NOS: 1

<210> SEQ ID NO 1
<211> LENGTH: 1647
<212> TYPE: DNA
<213> ORGANISM: Luciola filiformis yayeyamana

<400> SEQUENCE: 1
atggaaatgg aaaaggaaga gaatgttgtg tatggccctc agccattcta ccccattgaa      60
gcaggatccg caggaataca gttacataag tacatgcatc aatatgcaca acttggagca     120
atcgctttta gtaatgctct taccggagtt gatatttctt accaagaata ctttgatata     180
acgtgccgtc tagctgaggc catgaaaaat tatggtatga cgcaggaagg acgtattgct     240
ttgtgcagtg aaaattgtga agaattcttt attcctgtgg ttgctggtct ttacatcggg     300
gtaggtgttg cacctactaa tgaaatctac actctccgtg aattaaatca cagtttgggt     360
atcgcagaac cgactattgt attcagctcc agaaaaggct taccgaaagt tctggaagta     420
caaaaaaatg ttacatgtat caaaacaatt gtcatattag atagtaaagt aaactttgga     480
ggttacgatt gtgtagaaac tttcattaag aaaaatgtac cgtcaggttt tcaaccaagt     540
agctttaaac cgatggatgt taagaatcgt aaagaacacc ttgctctact tatgaattcc     600
tctggctcta ctggtctacc taaaggtgta caaattacac acgaaggcac tgttaccaga     660
ttctcacatg ccaggatcc catttacgga aatcaagttt cgcctggcac tgctatttta     720
accgtcgttc cattccacca tggattcggt atgtttacca ctttaggata ctttgcttgt     780
```

```
ggataccgtg ttgtcatgtt aacaaaattc gatgaagaac tattcttgaa aacgctgcaa        840
gactataaat gtaccagtgt gattcttgtg ccaacattat tcggcatcct taacaaaagt        900
gaattgatcg ataaatttga tttatctaat ctaactgaaa ttgcttctgg tggagctcct        960
ttggcaaagg aagttggtga agctgttgcc agacgattta atctacccgg catccgccag       1020
ggatacggtt taacagaaac gacatcggct ttcattatta ctccagaagg tgacgataaa       1080
cctggagcat ctgggaaagt agtacccttg ttcaaagtaa aagttattga tcttgacact       1140
aaaaaaacat tgggtgtcaa tcgacgagga gagatctgtg taaaaggacc tagtcttatg       1200
aaaggctatg ttcgtaatcc agaagcaaca aaagaaatta ttgatgatga aggctggatg       1260
cacactggcg atattggata ttacgatgag gacgaacatt tcttcattgt agatcgtttg       1320
aaatcattaa tcaaatacaa agggtaccag gtaccgcctg ctgaattaga atccgttctt       1380
ttgcaacatc caaatatatt tgacgctggt gtagctggtg tccccgatcc tgaagctggt       1440
gaacttccag gggctgtagt tgtattggaa aaaggaaaga ctatgaccga gaagcaaatt       1500
gtggaatacg ttaatagtca agtagtaaac cacaaacgtt tacgtggtgg cgttcgattt       1560
gtggatgaag taccaaaagg ccttactgga aaaattgatg ctaaagtaat tagagaaatc       1620
cttaagaaac cacaatccaa gatgtaa                                          1647
```